(12) United States Patent
Maughan

(10) Patent No.: US 7,172,739 B2
(45) Date of Patent: Feb. 6, 2007

(54) PROTEIN FRACTIONATION

(75) Inventor: David W. Maughan, Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 479 days.

(21) Appl. No.: 10/154,443

(22) Filed: May 22, 2002

(65) Prior Publication Data

US 2002/0192759 A1 Dec. 19, 2002

Related U.S. Application Data

(60) Provisional application No. 60/292,729, filed on May 22, 2001.

(51) Int. Cl.
*B01D 11/00* (2006.01)
*B01D 11/02* (2006.01)
*G01N 1/18* (2006.01)

(52) U.S. Cl. ............... 422/276; 422/255; 422/261; 435/40.5; 435/40.52

(58) Field of Classification Search .......... 435/91.1, 435/40.5, 40.52; 514/12; 210/23; 422/276, 422/255, 261
See application file for complete search history.

(56) References Cited

U.S. PATENT DOCUMENTS

| | | | |
|---|---|---|---|
| 3,883,425 A * | 5/1975 | Dorn | 435/2 |
| 4,590,002 A | 5/1986 | Zolton et al. | |
| 5,434,079 A | 7/1995 | Mozayeni | |
| 5,922,617 A | 7/1999 | Wang et al. | |
| 5,962,652 A | 10/1999 | Chu et al. | |
| 6,454,924 B2 | 9/2002 | Jedrzejewski et al. | |
| 6,632,655 B1 | 10/2003 | Mehta et al. | |
| 2001/0041357 A1 * | 11/2001 | Fouillet et al. | 435/91.1 |
| 2002/0192714 A1 | 12/2002 | Maughan | |
| 2004/0002456 A1 * | 1/2004 | Pathak | 514/12 |

OTHER PUBLICATIONS

J.M. Alderton and R.A. Steinhardt., "How Calcium Influx through Calcium Leak Channels is Responsible for the Elevated Levels of Calcium-dependent Proteolysis in Dystrophic Myotubes", *Trends Cardiovasc. Med*, 10:268-272, 2000.
S.R. Pennington and M.J. Dunn, "Proteomics: The Role of Proteomics in Meeting the Post-Genome Challenge", in *Proteomics: From Protein Sequence to Function*, pp. xvii-xxi, Eds. S.R. Pennington and M.J. Dunn, BIOS Scientific Publishers, Oxford, UK, 2001.
D.J. Cahill, et al., "Bridging Genomics and Proteomics", in *Proteomics: From Protein Sequence to Function*, Chapter 1, pp. 1-22, Eds. S.R. Pennington and M.J. Dunn, BIOS Scientific Publishers, Oxford, UK, 2001.
J.B. Bodensteiner and A.G. Engel, "Intracellular Calcium Accumulation in Duchenne Dystrophy and Other Myopathies: A Study of 567,000 Muscle Fibers in 114 Biopsies", *Neurology*, 28:439-446, 1978.
A. Pandey and M. Mann, "Proteomics to Study Genes and Genomes", *Nature*, 405:837-846, 2000.
R.J. Lipicky and J. Hess, "Potassium Permeability in Isolated Skeletal Muscle from Mice with Muscular Dystrophy", *American Journal of Physiology*, 226(3):592-596, 1974.
A.V. Hill, "Units, Definitions, Physical and Chemical Constants, Useful Quantities and Relations", in *Trails and Trials in Physiology: A Bibliography, 1909-1964; with Reviews of Certain Topics and Methods and a Reconnaissance for Further Research*, pp. 242-247, Edward Arnold Publishers, Ltd.
R.E. Godt and D. W. Maughan, "On the Composition of the Cytosol of Relaxed Skeletal Muscle of the Frog", *Am. J. Physiol*. 254 (Cell Physiol.23): C591-C604, 1988.
M. Wyss, et al. "Re-evaluation of the Structure and Physiological Function of Guanidino Kinases in Fruitfly (*Drosophila*), Sea Urchin (*Psammechinus Miliaris*) and Man", *Biochem. J.*, 309:255-261, 1995.
D. Maughan, et al., "Protein Separation of Cytosolic and Cytomatrix Fractions from Skinned Skeletal Muscle Fibers", *Biophysical Journal*, 49, 1986.
J. Warmke, et al., "Myosin Light Chain-2 Mutation Affects Flight, Wing Beat Frequency, and Indirect Flight Muscle Contraction Kinetics in *Drosophila*", *J. Cell Biol.*, 119(6):1523-1539, 1992.
R. Godt, et al. "Cytosol Constituents from Frog Skeletal Muscle Determined by Laser Microprobe Mass Analysis", *Journal of Physiology*, 371:160P, 1985.
D. Maughan, et al., "Approximating the Isometric Force-Calcium Relation of Intact Frog Muscle Using Skinned Fibers", *Biophysical Journal*, 69:1484-1490, 1995.

(Continued)

*Primary Examiner*—Mark L. Shibuya
(74) *Attorney, Agent, or Firm*—Wolf, Greenfield & Sacks, P.C.

(57) ABSTRACT

A method and apparatus for physically separating polypeptide constituents of a sample fluid by (a) providing a sample fluid comprising a mixture of polypeptides of differing physical and/or chemical properties; (b) contacting the fluid with at least two individual polymer matrix units, each polymer matrix unit preferentially accepting a different set of polypeptides on the basis of one or more physical and/or chemical properties; and (c) extracting the set of polypeptides from each polymer matrix unit.

14 Claims, 8 Drawing Sheets

OTHER PUBLICATIONS

R. Tohtong, et al, "Impairment of Muscle Function Caused by Mutations of Phosphorylation Sites in Myosin Regulatory Light Chain", *Nature*, 374:650-653, 1995.

D.W. Maughan and J. Vigoreaux, "An Integrated View of Insect Flight Muscle: Genes, Motor Molecules, and Motion", *News Physiol. Sci.*, 14:87-92, 1999.

D. Maughan and E. Wegner, "On the Organization and Diffusion of Glycolytic Enzymes in Skeletal Muscle", in, *Muscle Energetics*, pp. 137-147, Alan R. Liss, Inc., 1989.

D. Maughan, "Diffusible Magnesium in Frog Skeletal Muscle Cells", *Biophys. J.*, 43:75-80, 1983.

D. Maughan, "A New Method to Measure Intracellular Diffusible Elemental Concentration", in *Contractile Mechanisms in Muscle*, pp. 359-363, Eds. G.H. Pollack and H. Sugi, Plenum Publishing Corporation, 1984.

D. Maughan and C. Recchia, "Diffusible Sodium, Potassium, Magnesium, Calcium and Phosphorous in Frog Skeletal Muscle", *J. Physiol.*, 368;545-563, 1985.

D. Maughan and C. Lord, "Protein Diffusivities in Skinned Frog Skeletal Muscle Fibers", in *Molecular Mechanism of Muscle Contraction*, pp. 75-84, Eds. H. Sugi and G.H. Pollack, Plenum Publishing Corporation, 1988.

M.A.W. Andrews, et al., "Ion-specific and General Ionic Effects on Contraction of Skinned Fast-Twitch Skeletal Muscle from the Rabbit", *J. Gen. Physiol.*, 98:1105-1125, 1991.

D.W. Maughan and R.E. Godt, "Protein Osmotic Pressure and the State of Water in Frog Myoplasm", *Biophysical Journal*, 80:435-442, 2001.

D. Maughan and C. Lechene, "Microanalysis of Liquid Samples from Muscle Cells", *Fed. Proc.*, 39, No. 6, 1980.

D. Maughan, "Concentration of Diffusible Magnesium in Muscle Cells", *Fed. Proc.*, 41, No. 5, 1982.

D. Maughan and E. Wegner, "Diffusivity of Parvalbumin and Other Proteins in Freshly Skinned Frog Skeletal Muscle Fibers", *Biophysical Journal*, 51, 1987.

D. Maughan and E. Wegner, "Diffusion Coefficients of Cytosolic Proteins in Rabbit Muscle", *Biophysical Journal*, 53:61a, 1988.

D. Maughan and E. Wegner, "Concentrations of Glycolytic Proteins in Rabbit Psoas Muscle Fibers", *Biophysical Journal*, 55:266a, 1989.

D. Maughan, et al., "Glycolytic Enzyme Content in *Drosophila* Flight Muscle Lacking Actin", *Biophysical Journal*, 59:37a, 1991.

Brenner, S. et al., Gene expression analysis by massively parallel signature sequencing (MPSS) on microbead arrays. Nat Biotechnol. Jun. 2000;18(6):630-4. Erratum in: Nat Biotechnol Oct. 2000;18(10):1021.

Oleschuk, R.D. et al., Trapping of bead-based reagents within microfluidic systems: on-chip solid-phase extraction and electrochromatography. Anal Chem. Feb. 1, 2000;72(3):585-90.

Takei, N. et al., Monitoring of acetylcholine released from postnatal rat basal forebrain cholinergic neurons cultured on membrane filter by cell bed perfusion system and HPLC-ECD. Exp Neurol. Jun. 1990;108(3):229-31.

\* cited by examiner

Top view

Front view

PROTEIN FRACTIONATION

RELATED APPLICATIONS

This application claims priority under 35 U.S.C. §119 from U.S. provisional application Ser. No. 60/292,729, filed May 22, 2001.

1. GRANT INFORMATION

At least a portion of this work was supported by National Institutes of Health Grants AM33833 and AR38980. The United States Government may have limited rights to certain aspects of the invention described herein.

2. FIELD OF THE INVENTION

The invention relates to the field of proteomics, specifically to a method and apparatus for fractionating biological samples and aliquoting micro-scale polypeptide-containing fractions for subsequent chemical and/or physical analysis.

3. BACKGROUND OF THE INVENTION

Although the genomics era has produced an unprecedented amount of information relating to the genetic basis of biology, it is commonly understood that genetic information alone cannot fully elucidate the biological machinery of cells, tissues and organisms. Existing methods of genomic analysis cannot assign protein function based on gene sequence. Detection of RNA in tissue biopsies is hindered by rapid RNA degradation, and mRNAs present in low quantity are not readily measured. Even where quantitative analysis is possible, mRNA abundance is not always directly related to protein quantity. Protein content and activity are also affected by hundreds of post-translational modifications, and the activity of a specific protein is often related to its subcellular location. Neither protein content nor activity can be fully accounted for by genomic analysis.

For a thorough understanding of biological structure and function, it is necessary to complement genomic information with data elucidating the expression, structure, location (tissue, cellular, and subcellular) and activity of the vast array of proteins and peptides present in various fluids, cells, tissues, and organisms. The collection of such data is the realm of the field of proteomics, which complements genomics by systematically analyzing and documenting such information in healthy and diseased fluids, cells, tissues and organisms, and in the presence or absence of external stimuli, such as pharmaceuticals and toxic substances. Proteomics is rapidly becoming one of the most important contributors to biology and medicine in the post-genomic era. For recent reviews of the state of proteomics, see Pandey and Mann, "Proteomics to study genes and genomes" *Nature* 405:837–846 (2000); and see Pennington and Dunn, eds., *Proteomics: From Peptide Sequence to Function*, Bios Scientific Publishers (2001).

A successful proteomics platform requires the rapid, accurate and reproducible acquisition of vast amounts of raw data containing information about the presence and state of proteins in a given biological tissue sample. However, the proteomics field has suffered from the lack of technological advances that would facilitate such data collection.

3.1 Subcellular Fractionation and Protein Separation

A key requirement of a successful proteomics platform is the separation of complex mixtures of proteins obtained from biological fluids (e.g., serum, plasma, urine, CSF), cells, tissues, or whole organisms. The currently preferred method for accomplishing this task makes use of two-dimensional gel electrophoresis (2-DE). 2-DE is effective for separating thousands of proteins, but has significant limitations.

One such limitation relates to the need to compare 2-DE patterns in gels prepared in different labs. Accurate comparison can be quite difficult or even impossible. Salts and detergents used in 2-DE gels can create background signals which interfere with mass spectrometry (MS) analysis. Tissue samples are often processed for 2-DE analysis by breaking up frozen tissue; however, this process can make localization studies difficult. For adequate resolution of scarce proteins, 2-DE requires the use of relatively large samples (on the order of 10 mg or greater). Where the samples are biopsies, the need for larger samples increases tissue damage and discomfort in subjects undergoing biopsies.

Moreover, larger samples may not be possible in situations in which the diseased tissue is highly localized.

Current attempts to improve the speed and accuracy of proteomic analysis generally focus on improvements in 2-DE. In a recent book reviewing the state of the field, referring to 2-DE the editor stated: "[W]hilst the (2-DE) method has significant limitations it seems likely to remain unrivaled as a method to resolve large numbers of proteins for expression profiling and subsequent identification for some time to come." Pennington and Dunn, Introduction, *Proteomics: From Protein Sequence to Function*, Bios Scientific Publishers, p. xxi (2001).

One way to increase 2-DE throughput is by reducing gel size; however, smaller spot sizes result in smaller amounts of target proteins and decrease the ability to detect proteins present in small numbers.

4. SUMMARY OF THE INVENTION

The invention in some aspects provides a method for protein separation and analysis, which forms the basis of a new proteomics platform. Protein separation is generally the rate limiting step in proteomic data collection. The platform of the invention in some embodiments facilitates an increase of the rate of proteomic analysis by at least 2–3 orders of magnitude (depending upon the speed of the MS and data processing techniques employed). Unlike past attempts to speed proteomic analysis, the novel advances made by the inventor in the development of the present invention alleviate the need for reliance on 2-DE analysis.

The invention in some aspects relates to a method for fractionating a sample of biological cellular material to separate a subset of proteins and other cellular components from the cellular material. The general method involves flowing a fractionating solution through a perfusion chamber at a rate calculated to permit fractionation and equilibration of the subset of cellular components released by the fractionating solution, while collecting the protein-loaded solution as it flows out of the chamber for downstream processing and analysis. Alternatively, the method involves flowing a fractionating solution into the perfusion chamber and maintaining the solution in the chamber for a time sufficient to permit fractionation and equilibration of the sample. Protein-loaded fluid can then be flowed out of the chamber for downstream processing and analysis.

The outflow pores or ports of the perfusion chamber are preferably constructed so that when the protein-loaded fluid flows out of the chamber, a bubble or droplet of fluid (or an array of bubbles or droplets) is formed. Moreover, the bubble or droplet is preferably coated with oil or contained within an oil reservoir to prevent dehydration.

The sample of biological cellular material can be extremely small, and in some embodiments has a mass that is less than 10 mg, or in other embodiments less than 1 mg. In some embodiments, the sample is treated with a series of fractionating solutions, each fluid extracting a different set of proteins from the tissue. For example, the solutions may suitably include: (a) a solution which solubilizes plasma membrane while leaving membranes of intracellular organelles intact, thereby permitting cytosolic polypeptides and plasma membrane proteins (which diffuse into and equilibrate throughout the sample and fractionating solution volume) to be separated from the other cellular material; (b) a solution which solubilizes membranes of organelles, permitting organellar polypeptides to diffuse out of cells of the sample and to be separated from non-organellar cellular material; and (c) a solution which solubilizes cytomatrix polypeptides, permitting cytomatrix polypeptides to be separated from non-cytomatrix cellular material. For example, the solution that solubilizes plasma membrane may contain a detergent such as saponin, which, at low concentrations, preferentially solubilizes cholesterol-rich membranes. The solution that solubilizes other membranes, i.e., those of the intracellular organelles, may contain a detergent such as triton X100. The solution that solubilizes cytomatrix cellular material may contain solubilizers such as urea or cyanogen bromide.

The method for fractionating a sample may form a component of a larger method for physically separating polypeptides from an input composition. The larger method generally involves: (a) fractionating a sample of biological cellular material as described above; (b) simultaneously or sequentially introducing two or more polymer matrix units (PMUs) into the fluid to fractionate polypeptides on the basis of one or more physical or chemical properties; (d) contacting a substrate with one or more of the PMUs, or vice versa, to deposit one or more sample aliquots for chemical analysis.

The invention also relates to in some aspects a perfusion chamber device for fractionating a sample of biological cellular material to obtain a subset of polypeptides associated with specific cellular compartments of the cellular material. The device generally includes: (a) a perfusion chamber for holding the sample, the perfusion chamber having one or more inlet ports for permitting fluid to enter the chamber and one or more outlet ports for permitting fluid to exit the chamber; (b) a source of fractionating fluid and/or washing fluid in fluid communication with an inlet port; and (c) a means for forcing fluid from (b) into the perfusion chamber and out through the outlet port(s). Any one or more components of the device may be automated, and required movements may be performed robotically. The perfusion chamber device may be quite small. For instance the volume may be 10 µl or less, or even 1 µl or less. The shape of the perfusion chamber may vary widely. In general, it will be useful to tailor the shape and size of the perfusion chamber to the shape and size of the sample being analyzed. In some embodiments a generally spherical perfusion chamber is utilized.

The perfusion chamber may be coupled in selective fluid communication with a set of one or more reservoirs. The set of reservoirs preferably includes several subsets of one or more reservoirs, each subset comprising a fractionation solution. Moreover, the set may also comprise a subset of one or more reservoirs, each subset comprising a wash solution. Selection of the reservoir for flowing of fluid into the perfusion chamber may be automated, and may be physically controlled using common tubes, valves, pumps, switches and the like. Examples of fractionation solutions include: (a) a solution which solubilizes plasma membrane while leaving membranes of intracellular organelles intact, permitting cytosolic polypeptides and plasma membrane proteins to diffuse out of cells of the sample and to be separated from the other cellular material; (b) a solution which solubilizes membranes of organelles, permitting organellar polypeptides to diffuse out of cells of the sample and to be separated from non-organellar cellular material; and (c) a solution which solubilizes cytomatrix polypeptides, permitting cytomatrix polypeptides to be separated from non-cytomatrix cellular material. The solution that solubilizes the plasma membrane may, for example, be a detergent solution, such as a saponin solution.

The solution that solubilizes membranes of organelles may, for example, be another detergent solution, such as a triton X100 solution. The solution that solubilizes cytomatrix cellular material may, for example, be a urea or cyanogen bromide solution. In another aspect, the invention relates to a method of physically separating polypeptide constituents of a sample fluid, the method comprising: (a) providing a sample fluid comprising a mixture of polypeptides of differing physical and/or chemical properties; (b) contacting the fluid with at least two individual PMUs, each PMU preferentially accepting a different set of polypeptides on the basis of one or more physical and/or chemical properties; (c) extracting the set of polypeptides from each PMU. Step (c) may include depositing or blotting one or more sample aliquots on one or more substrates, said depositing being accomplished by simultaneously or sequentially bringing each PMU into contact with the substrate(s). The method steps may be automated, and movements may be performed robotically.

One aspect of the invention is that the sample fluid may be provided in very small amounts, e.g., about 10 µl or less, about 1 µl or less, or about 0.1 µl or less. The aliquots may also be provided on a micro-scale, e.g., about 100 pl or less of sample fluid, about 10 pl or less of sample fluid, or about 1 pl or less of sample fluid. Each PMU may have a size sufficient to permit the PMU to deposit at least one hundred 100 pl sample aliquots, at least one hundred 10 pl sample aliquots, or at least one hundred 1 pl sample aliquots. Hydration or equilibration typically occurs rapidly with these small volumes, for example taking less than 300 seconds to permit sufficient hydration or equilibration of the PMU to permit deposition of said sample aliquot(s). In some embodiments it requires less than 30 seconds or even less than about 3 seconds.

The PMUs can, for example, be used to separate polypeptides based on size, shape, hydrophobicity, and/or charge. The PMUs may be pre-hydrated, non-hydrated or dehydrated. They may be formed from a variety of polymers known in the art, such as polymers used in the manufacture of standard chromatography beads. The PMUs may be chromatography beads. Examples of suitable polymers include cross-linked dextrans and agaroses. The PMUs are preferably arranged in a 1D or 2D array, and may be provided as integral components of a substrate, such as a silicon chip.

The sample fluid may be provided on a macro-scale or a micro-scale. In some embodiments, the sample fluid is provided as a bubble or droplet or an array of bubbles or droplets. The sample fluid is treated to prevent dehydration, e.g. coated or surrounded with an oil to avoid dehydration.

Each PMU may be transported under oil from the sample fluid to the substrate. The substrate is suitably coated with a support film, such as a formvar resin. The support film may comprise additional compounds that facilitate chemical analysis. For example, the support film may comprise a substrate that preferentially absorbs ultraviolet laser light, thereby enhancing vaporization and ionization of polypeptides, e.g., 2,5-dihydroxybenzoic acid in ethanol or an analogous compound or mixture serving the same purpose. The support film may also suitably comprise an enzyme, such as trypsin, for digesting polypeptides in the sample aliquot. Furthermore, the support film may comprise an inhibitor, such as a protease inhibitor, to prevent degradation of sample polypeptide.

The sample aliquots may be deposited in a 1D or 2D array. The sample aliquots may be arranged in a grid format. Preferably, the substrate will comprise from about 20 to about 200 sample aliquots per square millimeter. The substrates may also be arranged in an array, so that the sample aliquots are arranged in an arrays-in-array format.

The PMUs may include units that fractionate according to size and/or shape. The PMUs may include uncharged units, so that valence of the polypeptide does not affect absorption. The PMUs may include anion exchanger units, which bind or attract negatively charged biomolecules. The PMUs may include cation exchanger units, which bind or attract positively charged biomolecules.

The invention also relates in some aspects to a method for fractionating polypeptides from a polypeptide source according to physical and/or chemical properties and analyzing said fractionated polypeptides, the method comprising: (a) providing a polypeptide source; (b) fractionating the polypeptide source to reduce the complexity of the polypeptide mixture and to provide a sample fluid; (c) fractionating the polypeptides as described above; and (d) chemically and/or physically analyzing one or more of sets of polypeptides produced in step (c). The polypeptide source can be any biological sample, but is preferably a biopsy, more preferably a needle biopsy. The mass of cellular material analyzed can be quite small, for example less than about 10 mg, less than about 1 mg, or about 0.1 mg (or less). The sample aliquot(s) can be treated with one or more organic solvents to create uniform residues of fractionated polypeptides. Multiple sample aliquots may be deposited from each PMU. Reference aliquots may be deposited for analysis alongside the sample aliquots.

The chemical analysis of the residues may be accomplished using any of a variety of analytical techniques known in the art, but will typically include a determination of mass to charge ratio. Techniques include but are not limited to various kinds of mass spectrometry (MS), preferably matrix-assisted laser desorption mass spectrometry (MALDI-MS). In MALDI-MS, each aliquot is subjected to laser desorption using a laser beam. An aspect of the present invention is that the single PMU method permits deposition of a sample aliquot that, when dried, yields a residue having a diameter that is less than the diameter of the laser beam. Deposition of such a small aliquot permits analysis of the entire aliquot, and thus permits more accurate quantification of sample content than has heretofore been possible. Mass spectrum amplitude may be correlated with amount of constituent polypeptide to provide a quantitative determination of amounts and concentrations of elemental isotopes and/or polypeptides in the sample aliquot(s). Calibration solutions may be analyzed alongside sample aliquots. The calibration solutions may suitably contain known quantities of marker polypeptides representing a cellular compartment. Known quantities of exogenous elements or chemical compounds may be added to the calibration and pre-fractionation solutions to serve as a standard for calculating sample volumes and/or polypeptide concentrations.

Output from the chemical and/or physical analyses may be transmitted to a computer processor for further analysis and/or stored in a database. Examples of suitable forms of analysis include: comparing mass/charge ratios of primary species with reference mass/charge ratios; comparing mass/charge ratios of fragmentation products with reference mass/charge ratios; and comparing mass/charge ratios of enzymatically digested peptides with reference mass/charge ratios. Difference spectra may also be obtained and assigned to polypeptides within a set of molecular weight ranges.

One aspect of the invention is that it does not require the use of gel electrophoresis; however, gel electrophoresis may be used to pre-process input samples to provide input fluid containing eluted polypeptides for further fractionation using the single PMU method.

The invention in other aspects also relates to a device for physically separating polypeptide constituents of a sample fluid, the device comprising: (a) at least two spatially separated PMUs, each PMU preferentially accepting the same or a different set of polypeptides separated on the basis of one or more physical and/or chemical properties; (b) a sample fluid exposing device for exposing the sample fluid in a manner which permits access by the spatially separated PMUs; (c) a substrate for receiving sample aliquots from the PMUs; (d) a mechanical movement device for mechanically contacting the PMUs with the sample fluid to preferentially load each PMU with a fraction of the sample fluid, and to contact the loaded PMUs with the substrate to deposit one or more fractionated aliquots on the substrate, wherein the mechanical movement device operates to achieve its purpose by mechanically moving any one or more of: (i) the PMUs; (ii) the sample fluid exposing device; and (iii) the substrate. The PMUs may be coated or otherwise surrounded with oil, except for that part in contact with the sample fluid. The sample fluid exposing device suitably comprises one or more chambers or wells, each holding a sample volume which in some embodiments is equal to or less than about 10 μl, equal to or less than about 1 μl, or equal to or less than about 0.1 μl. Each aliquot may be equal to or less than 100 pl of sample fluid, equal to or less than 10 pl of sample fluid, or equal to or less than about 1 pl of sample fluid. Each PMU may have a size sufficient to permit the PMU to deposit at least 100 100 pl sample aliquots, at least 100 10 pl sample aliquots, or at least 100 1 pl sample aliquots.

The mechanical movement device may suitably include or be electronically coupled to a computer programmed to control movement of the mechanical movement device. The computer may be programmed to maintain each PMU in the sample fluid for a time which in some embodiments is less than 300 seconds, less than 30 seconds, or less than 3 seconds. High throughput rates are achieved by fast robotic manipulation of samples in the fully integrated system of the invention.

The sample fluid exposing device suitably comprises a perfusion chamber. The perfusion chamber generally has one or more input ports for inserting biological sample(s), one or more input ports for flowing a fractionation fluid into the chamber, through and/or around the sample, and one or more output ports or pores for permitting fractionation fluid loaded with polypeptide from the sample to flow out of the perfusion chamber.

These and further aspects of the invention will be apparent to the skilled artisan from the Detailed Description of the Invention in Section 6, and the Examples in Section 7.

The terms "polypeptide" and "protein" are used in a generic sense to refer to linear or branched amino acid sequences of any length. For example, these terms include both peptides and proteins, as well as chemically modified proteins or peptides, such as glycoproteins, and include naturally occurring as well as non-naturally occurring amino acids.

In one aspect of the invention, methods for diagnosing a condition in a subject are provided. The methods include obtaining a biological sample of tissue or cells from a subject, fractionating the sample with the fractionation methods describe herein, and determining the amount of one or more specific cellular components in the sample. In some embodiments, the method further includes comparing the determination of the amount of specific cellular components in the sample and the amount of specific cellular components in a control group of cells as a diagnosis for a condition in the subject.

In one aspect of the invention, methods for determining onset, progression, or regression, of a disease in a subject are provided. The methods include obtaining a first biological sample of tissue or cells from a subject, fractionating the sample with the fractionation methods described herein, determining the amount of one or more specific cellular components in the sample, obtaining at a later time a second biological sample of tissue or cells from the subject, determining the amount of one or more of the specific cellular components in the sample, and comparing the determination of the one or more cellular components in the first sample and the second sample as a determination of the onset, progression, or regression of the disease.

In one aspect of the invention, methods for selecting a course of treatment of a subject having or suspected of having a disease are provided. The methods include obtaining from the subject a biological sample, fractionating the sample with the fractionation methods described herein, determining at least one cellular component in the sample that is associated with the disease, and selecting a course of treatment appropriate to the disease of the subject.

In yet another aspect of the invention methods for evaluating the effect of candidate pharmacological compounds on a disease cell phenotype are provided. The methods include obtaining a sample of cultured tissue or cells, fractionating the sample with the fractionation methods described herein, determining the amount of one or more specific cellular components in the sample, contacting the cultured tissue or cells with a candidate pharmacological agent, obtaining a second sample of the cultured tissue or cells, fractionating the second sample with the fractionation methods described herein, determining a second amount of one or more specific cellular components in the sample, and comparing the first and second amounts of one or more specific cellular components of the tissue or cells, wherein a change in the second amount of one or more specific cellular components, relative to the first amount of one or more specific cellular components, indicates the candidate pharmacological compound alters the amount of one or more specific cellular components indicating the onset of, progression of, or regression of a disease cell phenotype.

5. BRIEF DESCRIPTION OF THE DRAWINGS

Inset: Tracing of exemplar spectrum obtained from Co-doped, cytosol-loaded Sephadex G200 bead, illustrating a preferred method of calibrating spectral amplitudes using reference element standards. To quantify [Na], e.g., the integrated peak ratio of Na to Co in the cytosolic microsamples doped with 5 mM Co is compared to the corresponding ratio obtained from microsamples containing 5 mM Co and 0–15 mM Na. Arrow refers to ratio obtained from representative spectrum from frog cytosol, indicating that [Na] in this microsample is ~8 mM.

6. DETAILED DESCRIPTION OF THE INVENTION

Figure 1:
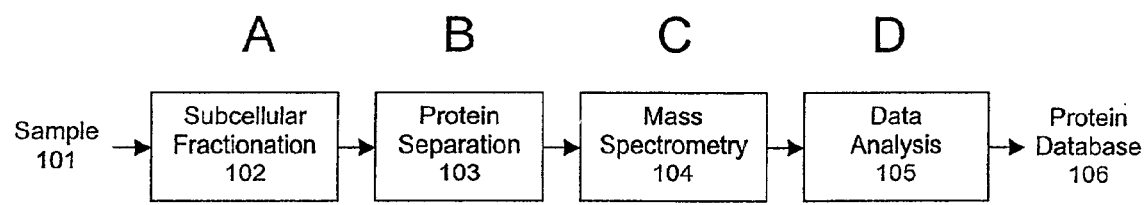
FIG. 1 illustrates the basic components of the proteomics platform of the invention.

FIG. 1 schematically illustrates the basic components of a generalized proteomics platform. A sample 101 (illustrated here as a tissue biopsy) is introduced at one end of the platform and the proteome of the sample is 'read out' into a protein database 106 at the other end for subsequent analysis. The sample is first subjected to subcellular fractionation procedures 102 designed to reduce the complexity of the protein mixture.

Next, each fraction of the sample is subjected to protein separation procedures 103 designed to further separate the proteins, e.g., on the basis of their physical and/or chemical characteristics. The sample is then chemically and/or physically analyzed, illustrated here by mass spectrometry step 104. Finally, the data from this chemical and/or physical analysis (e.g., mass-to-charge ratios of individual proteins and constituent peptides) may be subjected to an analysis step 105, in which the data is analyzed to identify and characterize the protein. Output from the data analysis step may be stored in a proteomic database 106 for subsequent analysis. The proteomics platform of the invention especially impacts each of the steps B–D.

6.1 Input Sample

The proteomics platform of the invention requires an input sample. The input sample can be any sample containing one or more polypeptides and may be, for example, a biological sample, such as sample containing:

a biological fluid (e.g., serum, urine, CSF, etc.);
cells (e.g., cultured cells, blood cells, etc.);
tissue (e.g., a biopsy); and/or
one or more whole organisms (e.g., unicellular or multicellular prokaryotic or eukaryotic organisms).

Alternatively, the sample may be a non-biological sample such as an in vitro generated library of proteins.

In one aspect of the invention, the proteomics platform of the invention is used to compare healthy and diseased input samples. In another aspect, input samples are analyzed to compare the biological impact of exposure to an external stimulus, such as a pharmaceutical compound or a toxic substance.

The input sample may be obtained using a variety of standard techniques known in the art. In one aspect of the invention, the biological sample is a tissue sample (e.g., a biopsy) obtained from a human or animal subject using a needle, bioptome, or other device for obtaining tissue samples.

6.2 Subcellular Fractionation

Pre-fractionation of proteins is one of the most important yet least developed aspects of modern proteomics. The goal of pre-fractionation is to divide the constellation of proteins in a proteome into at least one sub-constellation presenting a simpler problem for analysis. Though not strictly required for the practice of the invention, it is desirable for the division to occur along lines that have physiological meaning. The most widely practiced pre-fractionation procedures include separating whole-cell lysates into high or low salt precipitates and supernatant fractions. While these procedures achieve the aim of dividing the proteome, it is usually the case that cellular components are unavoidably intermingled.

The present invention provides a novel method of subcellular fractionation. The method makes use of a perfusion chamber. The perfusion chamber serves the purpose of containing a biological sample during subcellular fractionation procedures, and has a size and shape suited to this purpose. The material of the chamber is selected to ensure that chemical interaction with fractionation solutions does not eliminate the effectiveness of the chamber for its intended purpose. Alternatively, portions of the chamber exposed to such fractionation fluids may be coated with a protective coating. The chamber walls (or borders) include one or more openings that serve as input ports for insertion of biological sample(s) into the perfusion chamber. The chamber walls (or borders) also include one or more openings that serve as input ports for flowing a fractionation fluid into the chamber to contact the biological sample(s). The one or more openings for inserting biological sample(s) and one or more openings for flowing a fractionation fluid into the chamber may be the same ports, i.e., the sample material and fractionation fluid may enter the perfusion chamber by the same set of one or more ports. Additionally, the chamber walls (or borders) include one or more openings that serve as output ports for permitting fractionation fluid loaded with polypeptide from the sample to flow out of the perfusion chamber.

Figure 2:
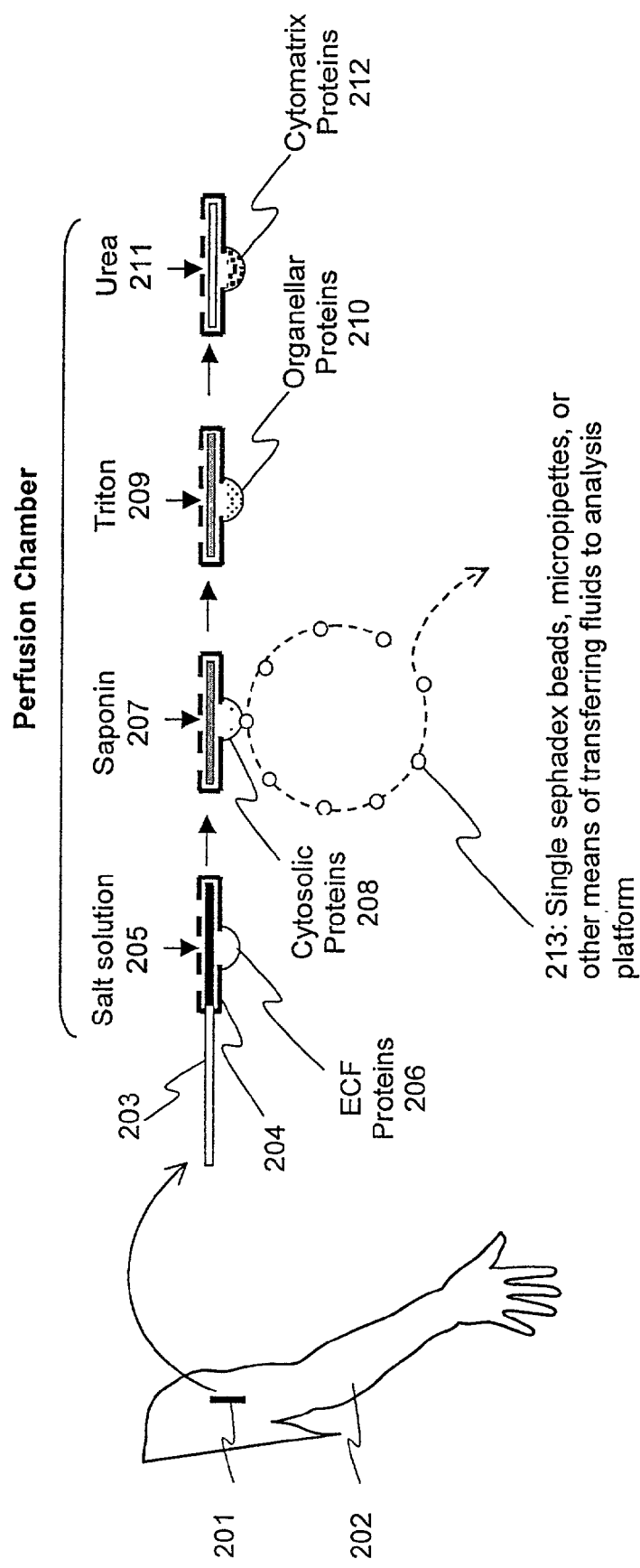
FIG. 2 illustrates a method aspect of the invention using a simple tubular perfusion chamber.

In a simple embodiment, the perfusion chamber is a tubular structure as illustrated in FIG. 2. The tubular structure 204 comprises an opening at one end that serves as an input port for insertion of the sample 201 (preferably a needle biopsy) into the perfusion chamber and may also serve as an input port for flowing fluids (e.g., cleaning fluids, fractionation fluids, etc.) into the perfusion chamber. The tubular structure 204 may include one or more openings that serve as exit ports along the length of the structure and/or at an end of the structure, through which fluids may exit the chamber.

In practice, a sample is inserted through an input port into the perfusion chamber. Fractionation fluid is flowed through an input port into the chamber, where it flows through and/or around the sample to release a fraction of the proteome of the sample. The loaded fractionation fluid flows out the exit port(s), where it can be collected for subsequent proteomic analysis. Collection of the loaded output fluid from the perfusion chamber can be accomplished by a variety of means known in the art, such as micro-pipettes, micro-tubes, or pins, but collection in some embodiments is accomplished by a single PMU according to the chromatography method described in Section 6.3.

In one embodiment, a series of fractionation solutions is introduced into the loaded perfusion chamber to systematically fractionate polypeptides from the sample. In this embodiment, polypeptides may be conveniently separated on the basis of their cellular or extracellular location. The introduction of the initial fractionation solution may be preceded by the introduction of a pre-fractionation (or wash) solution to remove extracellular fluid material or contaminants. This step is particularly useful where the sample is a tissue biopsy generally comprised of intact cells and some extra-cellular fluid material. Preferred pre-fractionation solutions include polypeptide-free ionic solutions designed to mimic the relevant extracellular fluid. A pre-fractionation solution appropriate for vertebrate muscle biopsies is standard Ringer's solution (Hill. *Trails and Trials in Physiology*. Edward Arnold, London, 1965). Likewise, the introduction of any subsequent fractionation solution may be followed by introduction of a wash (or cleaning) solution to remove residual cellular components released by the preceding fractionation solution. Preferred wash solutions include but are not limited to ionic solutions designed to mimic the relevant intracellular fluid compartment. An example for vertebrate muscle cytosol is standard Physiological Intracellular Solution (Maughan et al., "Approximating the isometric force-calcium relation of intact frog muscle using skinned fibers" Biophysical Journal 69: 1484–1490, 1995).

The operation of the subcellular fractionation aspect of the invention, using one embodiment, is illustrated by the example shown in FIG. 2. A tissue biopsy sample 201 is removed from a subject 202 using needle 203 and inserted into a perfusion chamber 204. Needle 203 is preferably of such a design as to allow the sample 201 to be directly captured and released from a narrow-bore blunt-end syringe. The sample 201 may be selected on the basis of morphological, cytological, or other physical or biochemical cues, from a larger biopsy obtained by conventional instruments, such as the Menghini or Silverman soft tissue biopsy needle, Bergstrom skeletal muscle biopsy needle, or cardiac muscle bioptome.

In the example illustrated in FIG. 2, four solutions are used to treat the sample: a saline solution 205, a saponin solution 207, a triton solution 209 and a urea solution 211. Additional/alternative solutions are known in the art.

An initial saline wash 205 is applied to remove extracellular fluid and proteins (plasma, lymph, or other fluids) from the sample 201. Fluid 206 containing the extracellular fluid and associated proteins exits the perfusion chamber via a port or pore. Fluid 206 may also contain a small fraction of cytosolic proteins from cells that have been disrupted during procurement of the biopsy. Each subsequent fractionation step is also optionally followed by a wash step.

The initial wash may be followed by treatment with a cytosolic protein-separating solution 207. This solution is preferably a physiological salt solution containing a detergent such as saponin. At sufficiently low concentration, saponin solubilizes the plasma membranes of cells in the sample 201 while leaving the membranes of the intracellular organelles intact. This step permits cytosolic proteins to diffuse out of the cell, thereby allowing these proteins to be separated from the remainder and to be identified with a cytosolic fraction 208.

Next, an organellar protein-separating solution 209 is introduced. This solution is preferably a physiological salt solution containing a detergent such as triton X100.

Triton solubilizes the membranes of intracellular organelles (e.g., in muscle: nuclei, sarcoplasmic reticulum, and mitochondria). This step permits organellar proteins to diffuse out of the cell, thereby allowing these proteins to be separated from the remainder and to be identified with an organellar fraction 210.

Finally, cytomatrix protein-separating solution 211 is applied. This solution may suitably contain urea, which solubilizes almost all cytomatrix proteins or cyanogen bromide or other similar solubizers. This step permits the remaining proteins to be taken up and identified with a cytomatrix fraction 212.

Each solution flows through the chamber 204, which holds the sample 201. The solution is infused into the chamber 204 at a rate selected to permit the solution to extract its target protein fraction. Alternatively, each solution may be introduced into the chamber and maintained in the chamber for a time sufficient to permit fractionation of the sample. As fractionation fluid is forced (or permitted to flow) through the chamber, it becomes loaded with polypeptides from the sample, facilitated by the short diffusion distances. Fluid loaded with polypeptide from a specific cellular compartment is permitted to exit or forced out of the chamber through one or more openings.

The fluid exits the chamber through one or more openings. Upon exiting the chamber, the fluid may form a bubble or droplet 206, 208, 210, 212 of polypeptide-loaded fluid on the surface of the chamber, as shown in FIG. 2. Alternatively, the fluid may exit the chamber and flow via one or more channels or tubes to another site where it is made available for aliquoting or for further fractionation. A layer of oil optionally protects the output fluid from evaporating. The size of the bubble and dilution factor depends on the relative amounts of solution added. The polypeptide-loaded fluid may be drawn into mini-pipettes or collected on pins, or preferably absorbed by PMUs 213 (see Section 6.3) or otherwise collected for subsequent analysis (see blocks B–D of FIG. 1).

The fluid bubbles or droplets 206, 208, 210, 212 may also be treated to enrich the fractionated proteins, e.g., by dehydrating the bubble or droplet. For example, such dehydration can be accomplished using a dense bead that does not absorb protein but does absorb water. By contacting the sample fluid with the dense polymeric bead, water can be removed, thereby concentrating proteins in the sample. A subsequent polymeric bead can be used to extract proteins from the sample, as described in Section 6.3, or the concentrated fluid may be stored or transported elsewhere for storage or for further analysis.

Fluid can be forced into the perfusion chamber using positive or negative pressure according to a variety of means known in the art, e.g., by use of a plunger or hydraulic system. In a highly simplified version, fluid is forced into the chamber by a syringe equipped with a plunger, coupled to an input port.

Figure 3A:
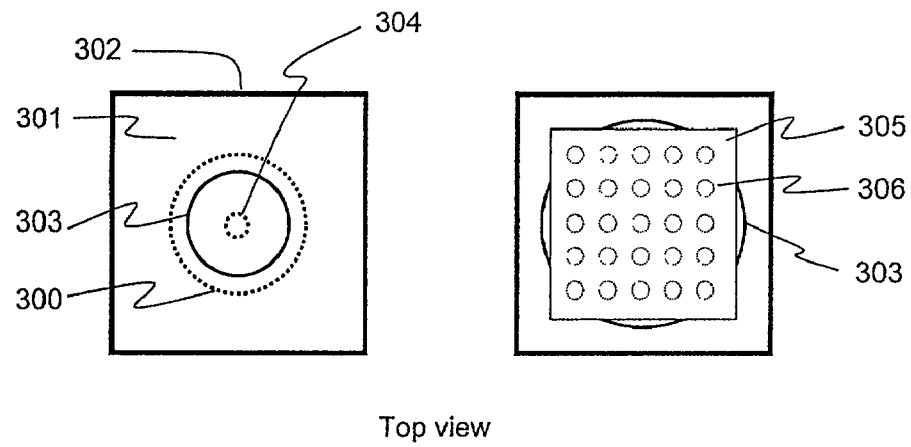
FIGS. 3A–3C illustrate the perfusion chamber (spherical form) aspect of the invention, illustrating design principles appropriate for rapid throughput.

In one embodiment, the perfusion chamber is a spherical structure 300 as shown in FIG. 3. FIG. 3A (left side) shows a top surface 301 of a block 302 housing the chamber 300, with a drop 303 of loaded fluid that has been forced through an opening 304 onto the top surface 301. Aliquots of drop 303 may be collected using a PMU array 305 of single PMUs 306 (right side; see Section 6.3); however, other means for collecting fluid aliquots from the top surface 301, such as micropipettes or pins, may also be used. The PMU array 305 compresses drop 303, expanding the diameter of the drop so all PMUs in the array are enveloped in fluid.

Figure 3B:
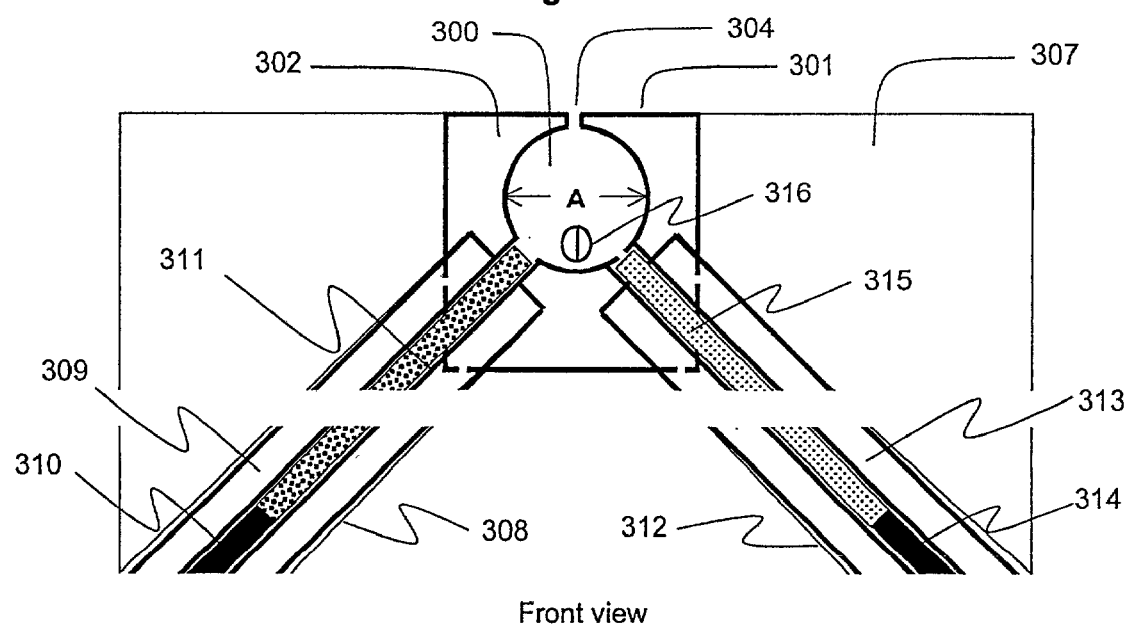

FIG. 3B shows a cross section of the spherical perfusion chamber 300 of FIG. 3A (e.g., dimension A is 830 μm for a 3 μl chamber containing a 2 μl sample). The perfusion chamber 300 in block 302 has an opening or pore 304 in the top surface 301, through which fluid can exit the perfusion chamber 300. Block 302 may be placed within a housing 307. Channel 308 provides a path for insertion of the sample, e.g., using a needle 309 and plunger 310 or a tube that contains sample 311. Channel 312 provides a path for insertion of a needle 313 and plunger 314, or, in a preferred embodiment of the invention, provides a fluid flow path coupled to a hydraulic system for injection of a wash or fractionation solution 315 into the chamber 300. The lengths of the columns of sample and solution are abbreviated in the illustration. One or more additional channels similar to channel 312 may be included to permit other solutions to be injected into the chamber 300. A seal, preferentially a pressure seal between needle and channel, e.g., facilitated by a taper to the channel in block 307, may be employed to prevent backflow of sample or solution into the channel. A microvalve 316, preferably a bicuspid valve consisting of a thin partition with a slit in the middle, may be employed at the interface between each solution channel and chamber 300. The valve allows solution to flow under pressure (positive or negative) into the chamber, while preventing material in the chamber from entering the solution channels. Fluid under pressure in the chamber flows out the opening 304. The chamber block 302 is preferably coated with, or constructed of, hydrophobic material. The bicuspid valve is preferably an integral component of the chamber block.

Figure 3C:
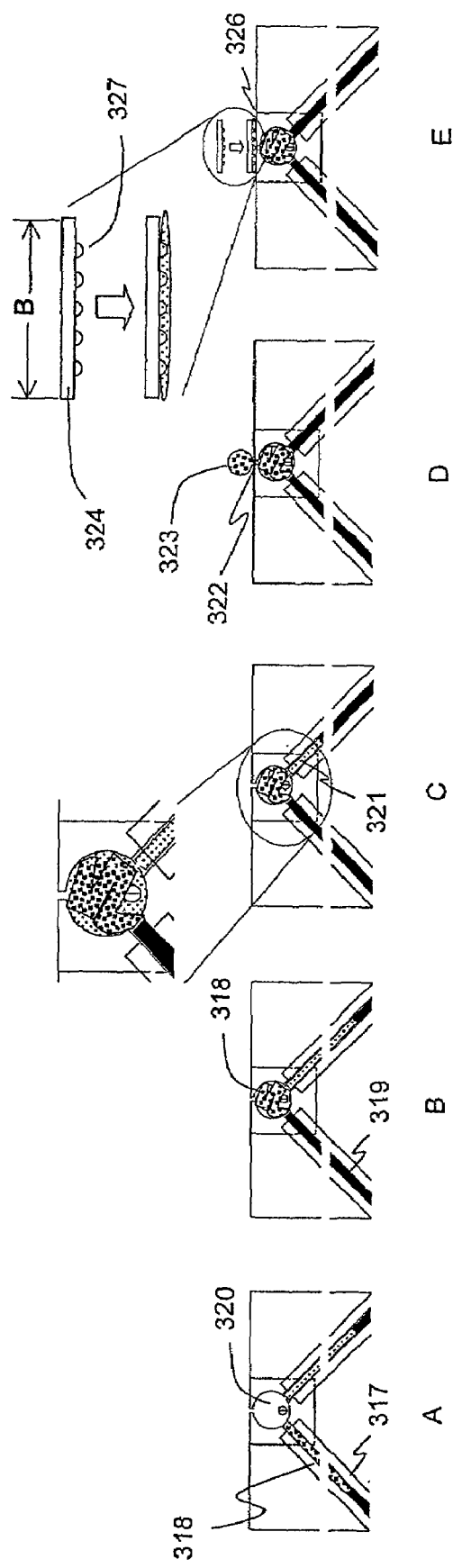

FIG. 3C illustrates the operation of a spherical perfusion chamber of the invention. In step A, the needle 317 with sample 318 is inserted in the channel. In step B, the plunger 319 forces sample 318 into chamber 320, where the sample volume may be one half that of the chamber. In step C, an aliquot of wash or fractionation solution 321 is forced into chamber 320 via one of the other openings. The volume of the wash or fractionation solution is optionally approximately equivalent to the volume of the sample. In step D, another aliquot of the same solution 321 is forced into the chamber after equilibration of the sample and solution in step C, at a rate that allows equilibration of the two aliquots of solution. The solution volume may be equivalent to that of the sample, thereby forcing a volume of wash or loaded fluid through the port or pore 322 to form a bubble or droplet 323. Finally, step E illustrates one embodiment, in which the drop is further fractionated using a square PMU array 324 (e.g., dimension B is 1.13 mm to match the scale of dimension A). Array 324 contacts the bubble or droplet 323 in a manner which flattens and spreads the sample on the surface 326 such that each PMU 327 of the PMU array 324 contacts the fluid and absorbs a fraction of polypeptides contained in the fluid.

In an automated embodiment, the perfusion chamber is a component of an automated system, in which any one or more of the steps discussed in this section are automated. For example, any one or more of the following steps may be suitably automated: opening or closing of any of the ports; insertion/removal of the sample material; flowing precise volumes of fluid into and out of the chamber; selection of a fluid flow path from the chamber to a wash or fractionation solution (e.g., using a rotary valve); and maintaining the sample in contact with the fractionation fluid for a time sufficient to ensure fractionation of target polypeptides.

The subcellular fractionation aspect of the invention allows whole tissue biopsies to be fractionated into submicroliter fluid samples, e.g., containing extracellular, cytosolic, organellar, or cytomatrix proteins. A given protein is thereby associated with a well-defined cellular compartment. Thus, the invention not only solves the problem of fractionating the proteome into smaller, more manageable units, the invention solves the problem of assigning proteins of each unit to a physiologically relevant cellular compartment. This information is of considerable value in research and diagnostics.

Another feature of the invention is that the method requires very little starting material. For instance, 0.1 mg or less, can be used, although larger masses can readily be used.

The minimum mass of starting material depends on the scaling factors used in the design of the chamber and the fraction volumes. A number of repeated assays can therefore be conducted using conventionally sized biopsy (i.e., from about 1 to about 100 mg). Since the sample size may be small, biopsies will result in far less collateral damage to surrounding tissue than current methods. This feature may be of considerable value in minimizing risk and discomfort to patients and research animals.

6.3 Single Polymer Matrix Unit Chromatography

The proteomics platform of the invention provides a novel single polymer matrix unit (PMU) chromatography aspect, already alluded to in Section 6.3. This aspect of the invention fractionates an input fluid to provide one or more output fluids with a simpler constellation of polypeptides than the constellation contained in the input fluid. Each PMU employed in this aspect of the invention preferentially excludes/accepts molecules on the basis of one or more physical or chemical characteristics, such as size, shape and/or charge.

Figure 4:
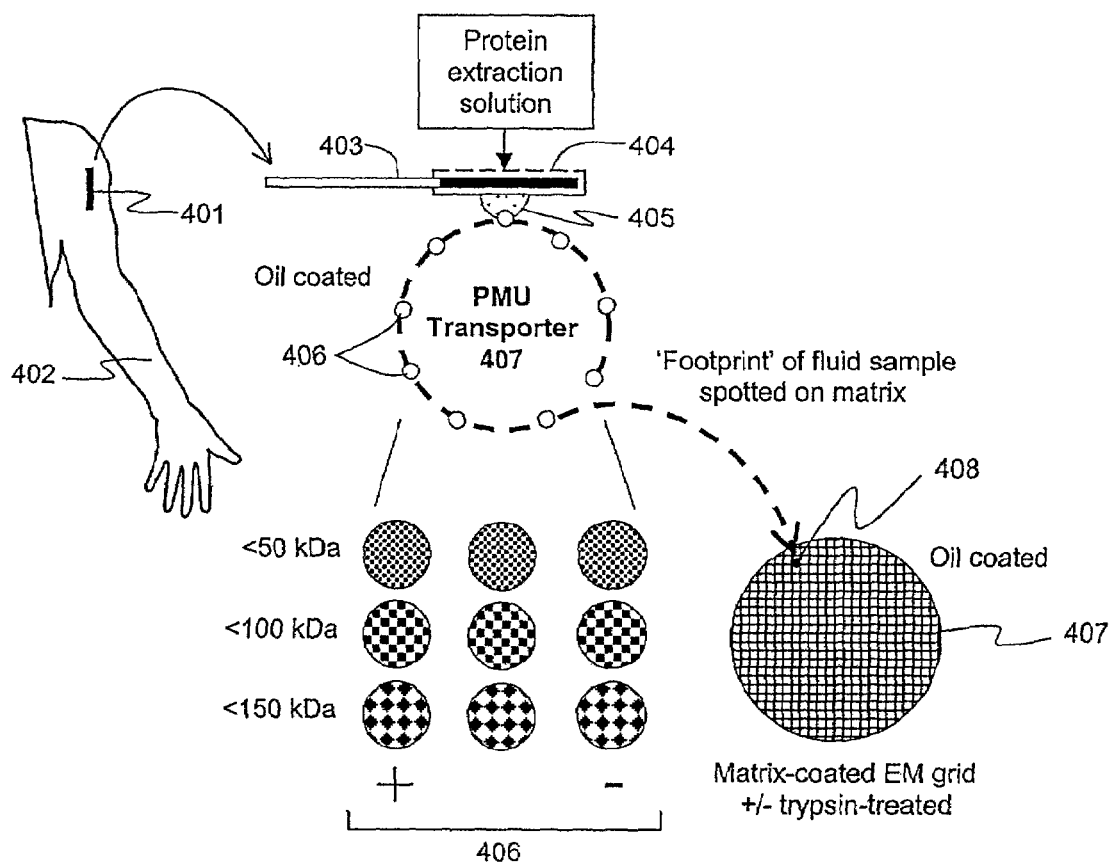
FIG. 4 illustrates protein separation by single bead chromatography.

The general PMU chromatography method is illustrated in FIG. 4. In this example, the input fluid 405 is prepared using the pre-fractionation procedure described in Section 6.2. A tissue biopsy 401 is removed from a subject 402 using needle 403 and inserted into a perfusion chamber 404. Alternatively, the input fluid can be any input fluid with a mixture of inorganic and organic compounds, such as polypeptides, and can be prepared from biological specimens according to a wide variety of known methods. Upon exiting the chamber 404, the fluid may form a bubble or droplet 405 of polypeptide-loaded fluid on the surface of the chamber, as shown in FIG. 4.

Enrichment or prefractionation techniques can be used to reduce the numbers of proteins in a sample prior to PMU chromatography. Suitable examples include chromatography, charge fractionation, and/or sub-cellular fractionation. As described above, enrichment by dehydration can be accomplished using a dense bead that does not absorb target protein but does absorb water.

The input fluid is fractionated using one or more PMUs 406. A preferred PMU is any of the wide variety of presently available chromatography beads, such as spherical Sephadex™ beads (Amersham Pharmacia Biotech AB, Uppsala Sweden). However, the PMU is not restricted to any particular shape or manufacturer, and may include any of a wide variety of customized chromatography beads. Preferred shapes are symmetrical shapes or shapes which can deposit a symmetrical, preferably circular aliquot when the PMU is contacted with a substrate. Examples of suitable shapes include: spherical, ovoid, cylindrical, conical, cubical, pill-shaped, and the like.

One example of PMU is a Sephadex™ bead. Sephadex™ beads are composed of a cross-linked dextran matrix and are available with a variety of porosities, chemical characteristics and molecular weight cut-offs (e.g., 10, 15, 25, 50, 75, 100, 150, and 200 kDa). Proteins with molecular weights below the cut-off value of each bead are preferentially absorbed by the PMU. Above the cut-off value, proteins are excluded.

The precise exclusion parameters depend on size and shape of the protein, as well as the physical-chemical properties of the bead. The reflection coefficients of the beads do not increase abruptly from 0 to 1 at the molecular weight cut-off, but rather increase from 0 to 1 over a narrow range of molecular weights around the cut-off values. G-series beads are uncharged, so the valence of the protein does not affect the distribution. Q-series beads are strong anion exchangers that attract negatively charged biomolecules. S-series beads are strong cation exchangers that attract positively charged biomolecules. GQ and SQ combinations are readily available for 25 and 50 kD cutoffs. Higher molecular weight GQ and SQ combinations may be custom ordered. Thus, a wide variety of Sephadex™ beads are available that may be used in the method of the invention to fractionate proteins and other biomolecules by size and net charge.

Each PMU 406 may be manually manipulated (simultaneously or sequentially) to contact a sample fluid to preferentially absorb a fraction containing one or more polypeptides having specific chemical and/or physical properties. However, the PMUs are preferably moved mechanically by a PMU transporter, such as a robotic device.

The PMUs are suitably mounted to a support, which is also referred to herein as a substrate, in 1D or 2D arrays. The arrays may contain multiple PMU sets, where each set contains one or more PMUs and the PMUs in a set are either of a common type or mixed. If of a common type, each set of PMU(s) extracts a different set of polypeptides from the input fluid. The support can be any material that does not chemically or physically interact with the input fluid in a manner that prevents effective operation of the PMUs.

The PMUs may be attached to the substrate by a variety of attachment means known in the art. The substrate preferably comprises an array of perforations, which may be suitably shaped and sized to permit the PMUs to fit snugly therein. A preferred method for attachment is to apply suction to the bottom side of the perforated array platform, dip the platform into a basin of beads presorted by size, then pick up the beads that are embedded in the perforations. Excess beads may be blown off the surface or otherwise removed. The PMUs may be further secured by a thin film of adhesive applied to the bottom side, which penetrates the perforations and adheres to the PMUs.

In an alternative embodiment, the PMUs may be integral components of the support. For example, standard manufacturing techniques can be used to create a silicon chip containing a 1D or 2D array of pores or openings in which the array of PMUs is mounted. The pores may extend through the wafer, in which case the PMUs can, for example, be cylindrical or pill-shaped (a cylinder with a half-sphere on one or both ends) units filling the pores and exposed to each side of the wafer. In one embodiment, the PMUs fill cylindrical channels in the chip, so that, when hydrated, they fill the channel and bulge out of the wafer. The resulting "chromatography chip" may be used to contact the sample fluid and then used to blot out samples. The chip can be exposed to the sample fluid on one side, and used to deposit aliquots on the opposite side. The side of the chip exposed to the input fluid may have channels etched in the chip (e.g., along rows of the PMUs) through which the input fluid can be flowed to bring the sample fluid into contact with the PMUs. The chromatography chip may be capped, e.g.

another silicon wafer or other material can be placed over the channels to enclose the channels so that fluid may be forced through the channels to contact the PMUs. The chips may include electric circuitry designed to create positive and/or negative charges in the vicinity of PMUs to facilitate migration of the polypeptides to and through selected PMUs.

Prior to exposure to the sample fluid, the PMUs may be dehydrated or hydrated, depending on the application. For example, dehydrated PMUs may be preferred if undiluted fluid samples are used, so that subsequent fluid aliquots can remain undiluted. Where the PMU is dehydrated, it is maintained in contact with the sample fluid for a period of time sufficient to permit the PMU to absorb an amount of fluid with an analyzable amount of polypeptide. Where the PMU is hydrated, it is maintained in contact with the sample fluid for a period of time sufficient to permit an analyzable amount of polypeptide from the sample to enter the hydrated PMU by diffusion. An analyzable amount is an amount that permits a chemical and/or physical characterization of one or more polypeptides from the PMU. In a preferred embodiment, the PMU contains sufficient polypeptide to permit at least one PMU from the PMU set to deposit a sample when contacted with a substrate, wherein the sample contains sufficient polypeptide to permit analysis of the sample by MALDI-MS.

The number of PMUs in an array may be limited by the relationship between the size and spacing of each hydrated PMU, the size and spacing of each fluid aliquot deposited on the substrate, the size of the substrate grid, and finally, the size (and volume) of the initial droplet of fractionated fluid. Assume, e.g., 1) that each hydrated PMUs is 80 µm diameter and that they are spaced orthogonally every 160 µm (center-to-center) in a 2D array; 2) that each hemispherical fluid aliquot is 20 µm diameter (assuming a volume of 2 pl), yielding a residue 20 µm diameter; and 3) that the aliquots are spaced orthogonally every 40 µm (c-t-c) on a 2D grid. A 5×5, 0.8 mm square PMU array, e.g., can interface with an initial (fractionated) sample fluid volume of 0.1 µl, e.g., if that volume formed a fluid disc 0.8 mm×1.414=1.13 mm diameter, and 0.1 mm deep (see FIG. 3, Section 6.2). The PMU can stamp out 25 aliquots on the substrate with each impression. Four sequential impressions in one direction, each shifted by 40 µm, followed by 4 sequential impressions in the orthogonal direction, each shifted by 40 µm, would yield one series of impressions that would yield (25×4)+(25×4)=200 aliquots covering an area approximately 1.04 mm square. Nine series of impression covering an area approximately 3.12 mm square would yield 200×9=1800 aliquots on a standard EM-sized substrate grid. Thus, a preferred number of PMUs used in a first generation array is about 25, with each array accommodating up to 25 different kinds of PMUs. Assuming 8 to 72 impressions per PMU (depending on the number of series carried out), the volume of sample and amount of protein reduced per PMU is 2 pl×(8 to 72)=16 to 144 pl. This range represents approximately 7–61% of the original sample fluid volume (i.e., 16 pl/235 pl to 144 pl/235 pl, assuming the diameter of the PMU is 80 µm hydrated and 40 µm dehydrated). Thus ample sample volume is available not only for multiple impressions from one PMU array, but for additional impressions from other PMU arrays.

This translates to extremely high efficiencies. In the example above, the utilization efficiency is as great as 61%, i.e., nearly 2 out of 3 molecules in the sample can be vaporized for MALDI-MS. Efficiencies of sample utilization using conventional protein fractionation methods prior to MALDI-MS are factors of $10^3$–$10^6$ lower. Referring again to FIG. 4, after contact with the sample fluid, as described above, at least part of the fraction of sample contained in each PMU 406 is transported, optionally with an oil coating or within an oil bath to prevent dehydration, to a mechanism or substrate 407 to deposit an aliquot 408 for chemical or physical analysis. In one embodiment, this step is performed by contacting the substrate 407 with a PMU 406 to deposit the sample aliquot 408. This blotting step is readily performed by a robotic, programmable device, which automatically brings each loaded PMU 406, one at a time or as a set, into contact with the substrate 407 to deposit sample aliquot (s) 408. PMUs 406 depicted in FIG. 4 preferentially exclude or accept molecules on the basis of one or more physical or chemical characteristics (e.g., size: <50 kDa, <100 kDa, <150 kDa; charge: +, –, or neutral).

An example of a substrate 407 is a substrate that is suitable for laser desorption mass spectrometry. Where the method of analysis of the sample is to be MALDI-MS, the size of the PMU and the contact pressure are preferably selected to deposit a sample with a diameter which is less than or equal to the diameter of the laser that will be used in the laser desorption step.

The substrate selected will depend on the type of chemical and/or physical analysis that the sample will undergo. The substrate must not be incompatible with the physical and chemical conditions of the analysis. Examples of suitable substrates are substrates constructed from metal (e.g., aluminum, beryllium, molybdenum, silver, stainless steel, titanium, and tungsten), diamond, pyrolytic carbon, carbon composite, and nylon. Such substances are commonly used in the construction of electron microscopy grids. A variety of grids is available commercially. For example, Electron Microscopy Sciences, Inc. (EMS Inc.: Fort Washington Pa.) supplies G400-series grids with 644 positions for liquid aliquots in a 3.05 mm diameter mesh of Co, Ni or Au. The substrate may be rectangular, to facilitate use of a two-dimensional array; however, conventional circular electron microscopy substrates may also be used.

Figure 5:
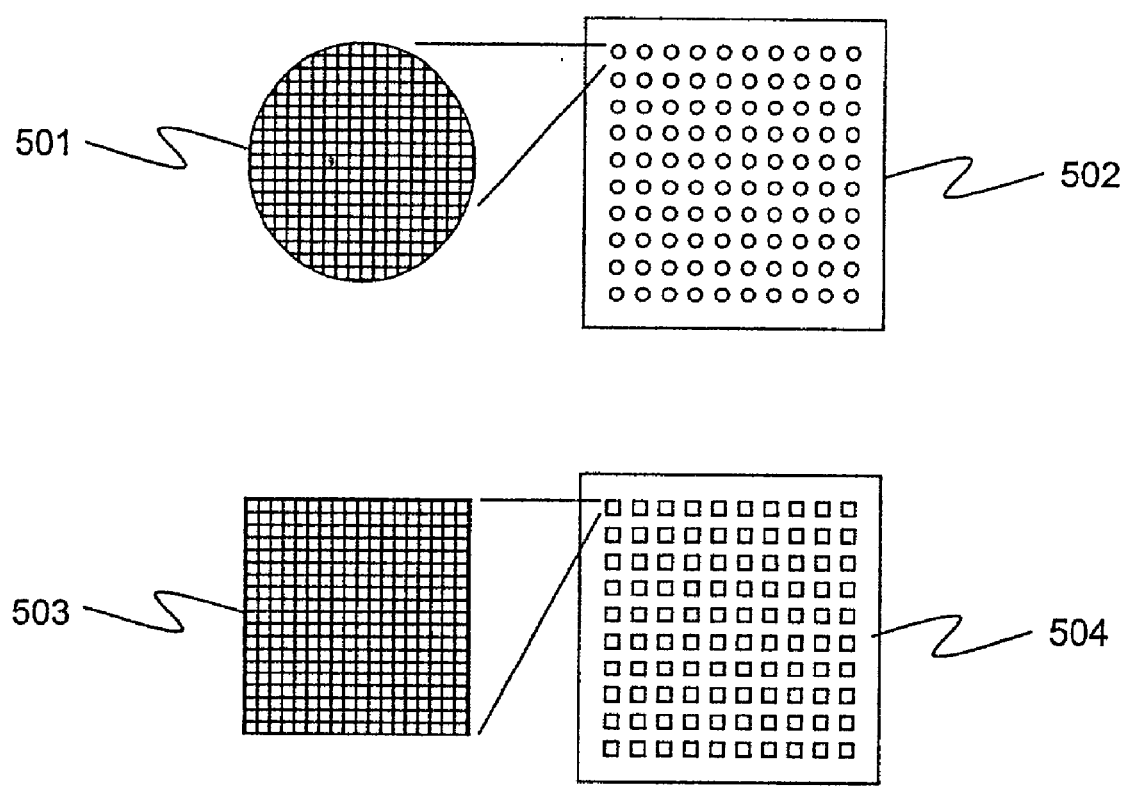
FIG. 5 illustrates the arrays-in-array platform of the invention.

An arrays-in-array configuration, as shown in FIG. 5, will facilitate rapid throughput. This aspect of the invention involves placing a PMU aliquot array 501 in a single well of a larger array 502, such as a conventional MALDI-MS array containing circular depressions or wells. However, a modified PMU aliquot array 503 placed in a square well array 504 is preferable, to maximize use of space in the wells. In the conventional approach, 1 liquid sample is placed in each well of a standard array (e.g., the Applied Biosystems (Foster City, Calif.) 100-well target plate for the Voyager-DE or -DE STR MALDI-TOF-MS; the Micromass (Manchester, UK) 120-well target plate for the Maldi MALDI-TOF-MS; or the Bruker Daltonics (Bremen, Del.) 100-well target plate for the Omni Flex or the 1536-well target plate for the REFLEX MALDI-TOF-MS). With an arrays-in-array configuration, EM-style grids contain, for example, 100–1000 defined positions with which to receive aliquots. As an example, a typical G-400 series grid from EMS Inc. can receive up to 644 spotted aliquots in defined positions. However, when the EM grids are placed in every well of the standard target plate, the arrays-in-array configuration increases the capacity of the target plate for sample aliquots by a factor of 644. As an example of the massive capacity of the system for high-throughput processing, the Bruker REFLEX target plate is capable of accommodating up to almost 1 million aliquots.

The substrate upon which the aliquots are deposited may be suitably coated with a support film, such as formvar resin, and may be treated with one or more chemical additives to facilitate the analysis. For example, support films are suitably pretreated with a small organic molecule (a matrix) that preferentially absorbs ultraviolet laser light, thereby enhancing the vaporization and ionization of peptides and proteins. A suitable composition for this purpose is 2,5-dihydroxybenzoic acid in ethanol. Other compounds are known in the art, which serve the same purpose. However, such pretreatment may be omitted where, for example, the method of the invention is employed for elemental analysis.

Support films may also be pre-treated with chemical reagents or enzymes such, as proteases or protease inhibitors that promote or prevent modification of the sample proteins. For example, the support film may comprise trypsin to facilitate trypsin digestion to cleave proteins into constituent peptides.

In one aspect of the invention, tiny aliquots of fluid are 'stamped out' by each PMU in a 1D, or preferably 2D array. Pilot studies have achieved up to 100 uniform 1 pl aliquots from a standard chromatography bead containing ~150pl fluid. Assuming 10 aliquots per bead in the example illustrated in FIG. 4, the fractionated, separated intracellular proteins of one biopsy sample 401 can be distributed among 2 pl aliquots 408 onto 270 squares (given 9 different beads 406 per sub-cellular fraction and 3 sub-cellular fractions 405 per biopsy). Assuming a 1:1 dilution at the initial fractionation step, the total volume of the initial fluid analyzed is 270 aliquots×1 pl=270 pl, or 0.27% of a nominal initial sample volume of 0.1 µl. Using such a small fraction of sample during the initial screening procedure allows the possibility of conducting other kinds of screens, using, e.g., other substrates with support films pre-treated with different chemical reagents or enzymes.

6.4 Chemical Analysis of Fractionated Proteins

Figure 6:
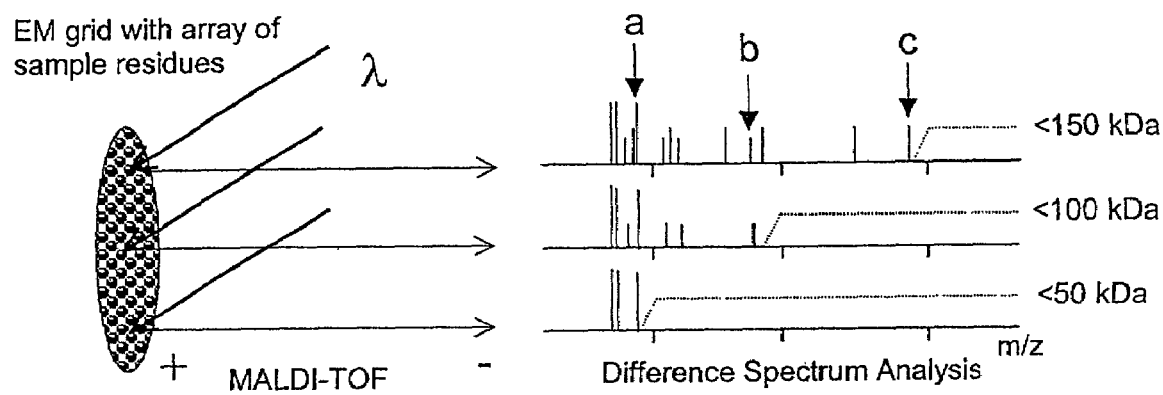
FIG. 6 illustrates a mass spectrometry and data analysis aspect of the invention.

The goal of the fractionation steps described in Sections 6.2 and 6.3 is to provide a sample for chemical analysis. One method of analysis is MS (FIG. 6). Prior to MS analysis, the fluid sample aliquots may be maintained on an oil-covered substrate. Oil may be removed by gently rinsing the target grid with a composition such as xylene, or preferably a non-toxic xylene substitute, which facilitates dehydration of the sample and the production of uniform spots of dried residue. The dried residues are preferably analyzed by MALDI-TOF spectrometry. For elemental analysis, the matrix can be omitted. Substrate handling and sample analysis is preferably conducted robotically. Various commercial mass spectrometers are available that can serve as suitable platforms (e.g., the Applied Biosystems Voyager-DE or -DE STR MALDI-TOF (Foster City, Calif.), the Bruker Daltonics Omni Flex and REFLEX MALDI-TOF (Bremen, Del.), and the Micromass MALDI MALDI-TOF (Manchester, UK)). These instruments can readily be modified to accommodate the invention. For example, modifications of the target plate holding the samples, the software controlling the laser light position, and the sample-tracking system can be made. Thus, in one aspect the invention relates to a modified mass spectrometer useful for accomplishing the methods of the invention.

Suitable modifications of the target plates can involve substituting the standard sample wells or depressions on the target plates with wells, depressions or stays that are designed, configured and fabricated in such a way that each mirco-array substrate grid, when inserted, is firmly secured to the target plate. Modifications of the software controlling the laser position would involve substituting the standard software with code that directs the laser light to specified coordinates, exactly duplicating those to which the PMUs were directed. Modifications of the sample-tracking system would involve adapting the standard indexing and cross-reference system to accommodate target plates with higher capacities.

One aspect of the invention is the use of residue spots that are completely vaporized by the laser because the diameter of the laser beam exceeds the diameter of the residue. Since all material is accounted for, it is therefore possible to correlate mass spectrum amplitude with amount of constituent protein under certain conditions (see below), thereby allowing quantitative determination of amounts and concentrations in the biopsy sample.

Figure 7:
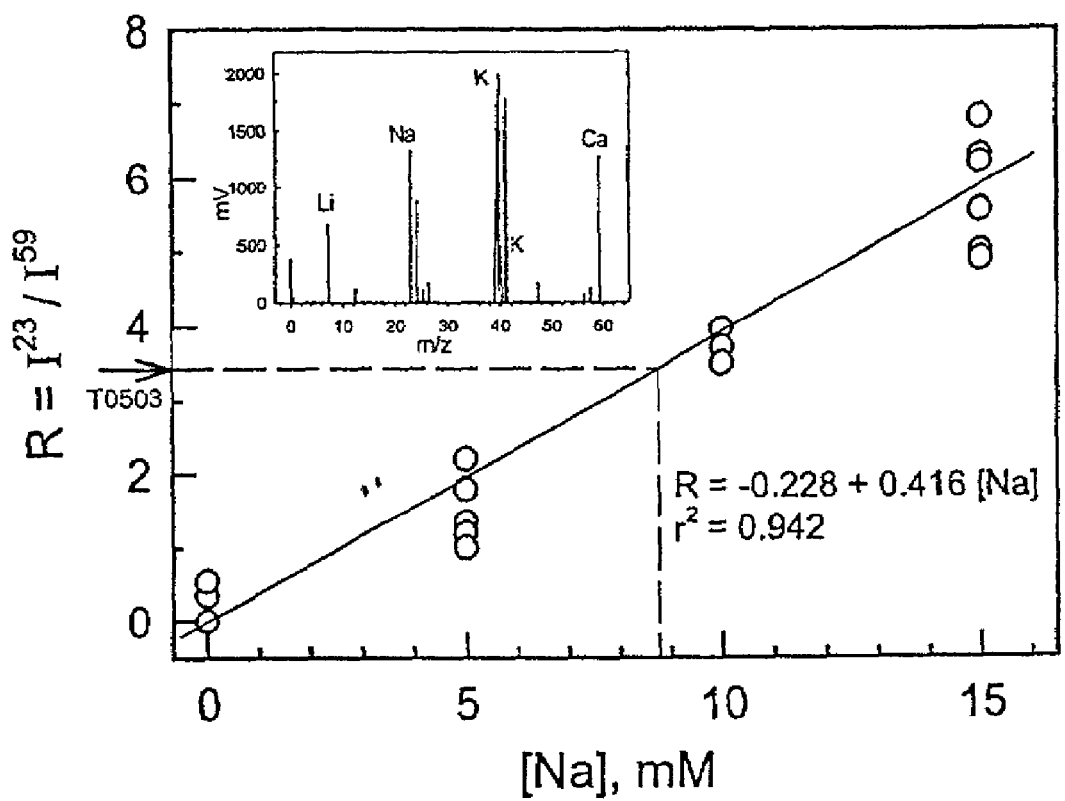
FIG. 7 illustrates the quantification of MS data using an exogenous reference standard.

Calibration solutions may be analyzed alongside sample aliquots. The calibration solutions may contain known quantities of marker polypeptides, e.g., polypeptides representing each cellular compartment. Known quantities of exogenous elements (such as Co) or compounds can be employed the calibration and pre-fractionation solutions (see FIG. 1, step A). The spectral amplitude of an exogenous element or compound provides a standard against which sample volumes and protein concentrations can be calibrated (e.g., see FIG. 7).

The invention may employ grid films with enzymes that enhance or inhibit digestion of fractionated proteins in fluid microsamples.

In addition to the foregoing, it should be noted that the single PMU method of the invention can be practiced in a multi-layered approach. For example, a sample fluid can first be fractionated using large PMUs (e.g., on the order of 10 nl). These large PMUs may then be used to deposit pools of fractionated fluid (e.g., in an oil-covered well plate). This fractionated fluid can then be further fractionated using smaller PMUs (e.g., on the order of 200 pl).

6.5 Data Analysis and Protein Database

Using an MS method, polypeptides or their tryptic products may be identified by their spectral fingerprints (mass/charge (m/z) ratios). For mixtures of polypeptides covering a broad range of molecular weights, the use of PMUs with different molecular weight cut-offs (slanted dotted lines, FIG. 6) allows difference spectra to be generated. Difference spectra represent the spectral fingerprint of polypeptides with a limited range of molecular weights. The more varied and widely distributed the molecular weight cut-offs (reflection coefficients) of the PMUs used, the more constrained the range of molecular weights of polypeptides represented by a given difference spectrum. Thus, one aspect of the invention is the use of difference spectra to simplify analysis of a complex mixture of polypeptides with native molecular weights spanning a broad range. Commercially available software may be modified to perform the data analysis and to store the information in a protein database.

FIG. 6 (right side) illustrates the use of difference spectra (highly schematic representation of fragmentation products or tryptic digests from 3 proteins). In this simple example, spectral lines obtained from a <50 kD cut-off bead represent a protein with the m/z ratio shown at arrow 'a' (40 kDa). Subtracting the <50 kDa spectrum from the <100 kDa spectrum yields the spectrum of a protein with the m/z ratio shown at arrow 'b' (85 kDa). Subtracting the <100 kDa spectrum from the <150 kDa spectrum yields the spectrum of a protein with the m/z ratio shown at arrow 'c' (135 kDa). The mass represents the molecular weight of the native form of the protein (rather than of monomeric subunits), because the protein is separated on the basis of its native size and shape. It must be emphasized, however, that, while difference spectroscopy can help corroborate identification of proteins by their exclusion from certain beads (primary identification is achieved by MS), difference spectroscopy is primarily intended to separate proteins into subsets based on native size, shape, and other characteristics depending on the beads used.

With respect to spectral analysis of metal elements (such as $^{23}$Na, $^{24}$Mg, $^{25}$Mg, $^{39}$K, $^{40}$Ca and $^{41}$K), single peaks represent contributions from all simple ions and molecular compounds of the metal element. Thus individual species, such as $Na^+$, $K^+$, $Mg^{2+}$, $Ca^{2+}$, and $PO^{4-}$ (or compounds of these species, including $MgATP^{2-}$ and creatine phosphate) cannot be specifically identified. Nevertheless, concentrations of some of the simpler metallic species can be estimated by assuming reasonable values for the concentrations and affinity constants of their primary moieties.

6.6 Diagnostics and Treatment

The invention involves in some aspects diagnosing or monitoring a disease by determining the presence of and/or level of at least one cellular component associated with the disease in a sample from a subject. In some important embodiments, this determination is performed by assaying a tissue sample from a subject using the methods described herein to determine at least one cellular component associated with the disease. As used herein, the terms "disease," "condition," and "disorder" are used interchangeably. As used herein, the term "marker" means a cellular component that is specifically associated with a disorder.

The invention also includes methods to monitor the onset, progression, or regression of a disease in a subject by, for example, obtaining cell or tissue samples at sequential times from a subject and assaying such samples to determine the presence and/or absence or change in level of a cellular component associated with the disease. A subject may be suspected of having a disease or may be believed not to have the disease. The sample can serve as a baseline level for comparison with subsequent cell or tissue samples from the subject.

The baseline level of a cellular component associated with a disease can be determined using standard methods known to those of skill in the art. Such methods include, for example, assaying a number of histologically normal cell or tissue samples from subjects that are clinically normal (i.e. do not have clinical signs of the disease) and determining the mean level of the cellular component in the samples. This baseline level can then be compared to the level of the cellular component in cells or tissues from a subject and a diagnosis of the disease can be made based on this comparison. The presence or absence of a disease as well as the severity of a disease can be determined based on the level of the cellular component in the subject sample as compared to that of a normal baseline level of the cellular component.

The presence of a disease-associated cellular component in a cell or tissue sample from a subject that is determined to be at a level above the baseline level for that cellular component, is diagnostic for a disease or condition in the subject. For example, muscular dystrophy can be diagnosed based on the identification of presence of abnormal dystrophin protein in a muscle sample from a subject using the methods of the invention. Similarly, the presence of a disease or condition may be indicated by the lack of a normal cellular component in a sample from a subject. For example, a lack of normal dystrophin in a muscle sample from a subject may be diagnostic of muscular dystrophy in that subject. The onset of a disease or condition in a subject may be indicated by the appearance of a marker(s) in a subject's samples where there was no such marker(s) determined previously. For example, if marker(s) for a disease or condition are determined not to be present in a first sample from a subject, the determination that the marker(s) are present in a second or subsequent sample from the subject is an indication of the onset of the disease in the subject.

Onset of a condition is the initiation of the physiological changes or characteristics associated with the disease in a subject. Such changes may be evidenced by physiological symptoms, or may be clinically asymptomatic. For example, the onset of a muscle wasting disease, or cancer may be followed by a period during which there may be disease-associated physiological characteristics in the subject, even though clinical symptoms may not be evident at that time. The progression of a condition follows onset and is the advancement of the physiological characteristics of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

Progression and regression of a disease or condition are indicated by the increase or decrease, respectively, of marker (s) in a subject's samples over time. For example, if marker (s) for a disease are determined to be present in a first sample from a subject and additional marker(s) or more of the initial marker(s) for the disease are determined to be present in a second or subsequent sample from the subject, it indicates the progression of the disease. Regression of the disease may be indicated by finding that marker(s) determined to be present in a sample from a subject are not determined to be found, or are found at lower amounts in a second or subsequent sample from the subject. Such a decrease may be indicative of success of treatment of the subject's condition or disease, which was begun prior to determination of the marker in the second or subsequent sample from the subject.

The progression and regression of a disease or condition may also be indicated based on characteristics of the cellular components determined in the subject. Some disease-associated cellular components may be abnormally expressed at specific stages of the disease or condition. (e.g. early-stage disease-associated cellular components; mid-stage disease-associated cellular components; and late-stage disease-associated cellular components). An example of this, although not intended to be limiting, is that cancer-associated cellular components may be differentially expressed in primary tumors versus metastases, thereby the stage and/or diagnostic level of the disease to be established, based on the identification of selected cancer-associated cellular components in a subject sample.

Treatment regimens can be selected or optimized for individual subjects using the methods of the invention. Different diseases are associated with different cellular components, and as described herein, the presence and/or levels of such cellular components can be determined using methods of the invention. On the basis of such a diagnosis of a disease or condition in a subject, one of reasonable skill in the art will be able to select treatment options and strategies to optimally treat or prevent the disease in a subject.

In addition, different types of diseases that can affect a single tissue type may express different disease-associated cellular components, or may have different spatial or temporal patterns. Such variations may allow disease-specific diagnosis and subsequent treatment tailored to the patient's specific condition. For example, various types of breast cancer [e.g. ductal carcinoma in situ (DCIS), invasive ductal carcinoma (IDC), invasive lobular carcinoma (ILC), invasive pleomorphic lobular carcinoma, inflammatory breast cancer, medullary carcinoma, mucinous carcinoma (also known as colloid carcinoma), and adenocarcinoma], may differ in that the expression of disease-associated cellular components may be specific for a given type of cancer. For example, in a plurality of subjects with DCIS, a temporal pattern of expression or level of expression of a cancer-associated cellular component may be identified, that differs from the temporal pattern of expression or level of expression of the same cancer-associated cellular component in IDC. These differences in expression, can enable a physician to diagnose the cancer on the basis of differential expression of the cancer-associated cellular components, and permits specific treatments to be selected and administered on the basis of the differential identification of the components.

The determination of whether treatment of a disease in a subject is effective, and/or whether the amount of a treatment administered is therapeutically effective can be done using methods of the invention. For example, diagnostic tests described herein, can be used to assess the disease status of a subject and evaluate the effectiveness of a pharmaceutical compound or agent that has been administered to the subject as a treatment. A first determination of the disease can be obtained using one of the methods described herein, and a subsequent determination of the presence of the disease marker in a subject may be done. A comparison of the presence of the disease, for example by determining the presence or level of a cellular component associated with the disease may be used to assess the effectiveness of administration of a pharmaceutical compound as a prophylactic or a treatment of the disease. A level of the cellular components associated with the disease that is above the baseline control level of expression for that tissue may be an indication of a need for treatment intervention by administering a different pharmaceutical compound or a different amount of the compound described herein to prevent or treat the disease.

In another embodiment, novel pharmacological compounds useful in the treatment of diseases or conditions can be identified by assessing variations in the presence or levels of cellular components associated with the disease, prior to and after contacting the diseased cells or tissues with candidate pharmacological compounds for the treatment of the disease. The cells may be grown in culture (e.g. from a cell line), or may be obtained from a subject, (e.g. in a clinical trial of candidate pharmacological compounds to treat the disease). Alterations in the presence or level of a cellular component associated with the disease, in diseased cells or tissues tested before and after contact with a candidate pharmacological compound to treat the disease, indicate progression, regression, or stasis of the disease thereby indicating efficacy of candidate agents and concomitant identification of lead compounds for therapeutic use in the disease or condition.

A pharmaceutical compound may encompass numerous chemical classes, although typically they are organic compounds. The candidate pharmacological compounds may be, for instance, small organic compounds, i.e., those having a molecular weight of more than 50 yet less than about 2500, preferably less than about 1000 and, more preferably, less than about 500. Pharmaceutical compounds may also be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Pharmaceutical compounds may be obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like.

Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known pharmacological compounds may be subjected to directed or random chemical modifications such as acylation, alkylation, esterification, amidification, etc. to produce structural analogs of the compounds.

6.7 Conclusions

The single PMU chromatography aspect of the invention may complement a variety of other established methods that allow proteins to be separated on the basis of their physical and/or chemical properties. The invention complements these currently available methods by providing a rapid, quantitative protein screen for high-throughput proteomics applications, with numerous advantages over currently used methods.

The novel proteomics platform of the invention has applications across the broad field of proteomics. The system can be automated to provide high throughput proteomic analysis of biological samples. Large amounts of data can be collected using the novel method and apparatus of the invention, and analyzed using known methods, e.g., to provide qualitative and quantitative assessments of changes in protein synthesis patterns or post-translational modifications between different tissues, between cells with different phenotypic or genotypic expressions, between healthy and diseased cells, and between cells or tissues treated with pharmaceutical compounds or other therapeutic treatments.

In this last regard, the method and apparatus of the invention can be used to identify and evaluate drug targets, to study mechanisms of drug action, and to study pharmacological and/or toxicological effects.

7. EXAMPLES

The ensuing non-limiting examples are illustrative of the practice of the invention.

7.1 Example 1

Single Sephadex Bead Protein Analysis of a Complex Mixture

Summary: A feasibility study using single Sephadex beads for protein analysis was carried out on biopsies of frog skeletal muscle. The results demonstrate that cytosolic proteins can be separated from other muscle proteins using single Sephadex beads. Two exemplar cytosolic proteins, creatine kinase and parvalbumin, were identified alongside purified protein standards, and their concentrations determined, using 1-D SDS PAGE.

The results support the utility of using single Sephadex beads for capturing relatively undiluted protein samples of intracellular fluid.

Materials and Methods: Bundles of 10–30 fibers were cut from the isolated semitendinosus muscle of *Rana temporaria*. The bundles were blotted and placed in a glass-bottom dish filled with mineral oil. The temperature of the oil and bundle was maintained at 4° C. using a thermoelectric device. Fiber segments were isolated by first subdividing the bundle, then manually stripping (skinning) the sarcolemma from a single fiber with a needle. The skinned fibers were straightened, cut to 2–4 mm length (segment diameter, ~0.1 mm), and moved to a clear region of the dish.

Dry Sephadex G-200 beads (diameter, 40 um) were placed onto the surfaces of the skinned fibers. Within 15 min, the beads absorbed up to 0.5 nl of cytosolic fluid. The beads were removed, placed in SDS-sample buffer, and absorbed proteins separated by 1-D SDS PAGE. The protein bands were silver stained alongside standards of purified creatine kinase and parvalbumin, and their amounts quantified by densitometry.

Results: The average concentrations of cytosolic creatine kinase and two isoforms of parvalbumin obtained from the single Sephadex beads are given in Table 1. The latter values were not significantly different than those obtained from parallel experiments in which we measured the concentrations of cytosolic proteins that diffused out of skinned fiber into the solution, thereby demonstrating that single beads can absorb cytosolic proteins (for accurate determination of protein concentrations, in may be necessary to measure the reflection coefficient profile of each bead type: see FIG. 6). The additional creatine kinase obtained by incubating the fiber in a large volume probably reflected extraction of cytomatrix-bound creatine kinase. This result suggests that an extended incubation in a relatively large volume of solution may have lead to extraction of cytomatrix proteins or cytomatrix-associated proteins like creatine kinase, whereas equilibration of the muscle cytosol with a relatively small volume of solution may not, thereby underscoring the importance of keeping wash and extraction solution volumes to a minimum in subcellular fractionation methodologies.

Table 1. Cytosolic concentrations of two proteins obtained from single Sephadex bead analysis of frog muscle. Means±S.D.

| Protein | Sampling method | Concentration (mg/ml) |
| --- | --- | --- |
| Creatine kinase | bead (i.e., diffusion into small volume) | 2.2 ± 0.7 |
|  | fiber (i.e., diffusion into large volume) | 8.8 ± 4.4* |
| Parvalbumin Iva | Bead | 3.0 ± 1.2 |
|  | Fiber | 4.6 ± 2.3 |
| Parvalbumin Ivb | Bead | 2.6 ± 1.1 |
|  | Fiber | 3.4 ± 3.4 |

*Difference significant at p <0.001.

7.2 Example 2

Elemental Mass Spectral Analysis of Vertebrate Muscle Cytosol

Summary: A feasibility study of elemental mass spectral analysis was carried out on a complex mixture of proteins from biopsies of frog skeletal muscle. Cytosolic fluid samples (50–200 µl) were obtained by placing dry G-200 Sephadex beads on the surface of single skinned muscle fibers under oil, and allowing the beads to directly absorb small volumes of cytosolic fluid. Microsamples (1–5 µl) of the absorbed fluid in the beads were then blotted onto suitable substrates and analyzed by laser mass spectrometry. Distinct spectra from inorganic ionic species and organic compounds (and their pyrolytic fragments) were obtained over a broad range of molecular weight-to-charge ratios (0–2400 amu). The concentration of Na was determined using a method of doping the sample with a known concentration of Co, and comparing the spectral amplitudes of Na and Co with a calibration curve generated using known concentrations of Na and Co. The results support the utility of the method.

Materials and Methods: Single muscle fibers from the *Rana temporaria* semitendinosus muscle were isolated and skinned under oil as in Example 1. Cytosolic fluid samples (50–200 pl) were obtained by placing dry G-200 Sephadex beads on the surface of the single skinned muscle fibers. After sufficient time (1–5 min) was allowed for absorption of cytosolic fluid, microsamples (1–10 µl) of the fluid in the bead were blotted onto oil-covered Formvar-coated electron microscopy grids. The beads were held and manipulated with the aid of a suction pipette and micromanipulator. A vertical stop on the manipulator allowed a predetermined amount of fluid (e.g., 10 pl) to be squeezed from the bead during each blot. After the blots were allowed to dehydrate (oil absorbs small amounts of water), the oil was removed from the Formvar substrate with xylene. The sample residues remaining on the dehydrated substrate were thin, circular, and nearly homogeneous deposits of cytosolic material.

Results: Sample residues were analyzed by a time-of-flight laser microprobe mass spectrometer (LAMMA 500, Leybold-Heraeus GmbH (Cologne, Germany). Molecular species of 0–2400 amu can be detected with this instrument, which ionizes and fragments the molecular species present in the sample by vaporization of the sample material with the incident laser beam. These preliminary tests, were focused on spectra in the lower mass/charge range; thus, no UV-absorbing matrix was used that would otherwise obscure the low-end spectra. The positive (anode end) spectra yielded reproducible peaks, which corresponded to isotopes of intracellular metals Na, Mg, K and Ca (at 23, 24–26, 39 & 41, and 40 amu: for example, see Godt et al., 1985). Prominent peaks from unidentified species were also seen reproducibly in the higher mass/charge range. The negative (cathode end) spectra also yielded a number of reproducible peaks.

In exploring ways to calibrate the LAMMA spectra, the variation in signal amplitude was examined in 1) replicate spectra taken from a single microsample, and 2) replicate spectra taken from multiple samples containing fluid of the same composition. Because each residue spot was completely vaporized by the laser (the diameter of the laser spot exceeded that of the residue), reproducibility of signal amplitude was excellent (e.g., normalized mean±S.D., 1.00±0.07 for Na and Co signal amplitudes, 15 mM [Na], FIG. 7). As expected, no detectable variation in mass/charge ratios was observed. Spectral amplitudes were related to the amount of species by equilibrating each bead containing cytosolic fluid with a similar bead containing a 10 mM cobalt reference standard. Results from the Co-doped cytosol bead were compared with those from Co-doped standard beads containing known concentrations of a given molecule. To quantify elemental [Na], for example, the integrated peak of Na was compared to that of Co in the Co-doped cytosolic microsamples (FIG. 7), and the resulting ratio was then compared to corresponding ratios obtained from calibration microsamples containing 5 mM Co and 0–20 mM Na.

Comparing amplitude ratios appeared to factor out most of the random variation observed in replicate spectra. Preliminary results using this approach indicated that cytosolic [Na] in freshly isolated muscle fibers is ~8 mM (e.g., see FIG. 7), consistent with values reported in the literature using other methods (see Godt & Maughan, 1988, and references therein).

7.3 Example 3

Subcellular Fractionation, Single Sephadex Bead Chromatography, and Mass Spectral Analysis of Proteins in Muscle Biopsies.

Summary: The invention is used to study complex mixtures of proteins from subcellular compartments of biopsy samples obtained from animal models. For example, aspects of the invention yield significant information about the composition of muscle cells. The goal is to determine the proteomes of specific types of muscles in animal models commonly used in muscle research. The proteome of muscle tissue from animals with specific protein alterations is compared with the proteome of muscles from wild type animals.

As discussed in Section 3 above, proteomics can be broadly defined as the systematic analysis and documentation of all the proteins in a biological sample. This field can be viewed as "a mass-screening approach to molecular biology, which aims to document the overall distribution of proteins in cells, to identify and characterize the individual proteins of interest, and ultimately to elucidate their relationships and functional roles" (Cahill et al., 2001). In order to address tractable problems and to restrict the analysis to manageable scales, the initial proteomic effort is be limited to muscles of the fruit fly and mouse, i.e., to striated muscle found in these standard laboratory species widely used in biological research whose genome can be readily manipulated to produce mutant strains. Muscles relevant to the academic interests of the primary investigators can be used (flight muscles in the fly and skeletal muscles in the mouse). However, in subsequent studies, the proteomics platform of the invention is used to analyze samples from other organisms, including mammals, e.g., humans. These subsequent analyses can be used to ascribe a molecular basis of performance differences among individuals in natural populations.

Materials and Methods:

Studies are carried out on complex mixtures of proteins from subcellular compartments of biopsy samples obtained from invertebrate and vertebrate animal models (muscle tissue from flies and mice). In both animal models, single muscle fibers are isolated and skinned under oil according to the methods described in the examples above. Subcellular fractionation of proteins and single bead chromatography are carried out as described in Examples 1 and 2, and MALDI-TOF analysis of the fractionated sample aliquots are carried out using standard procedures, using manual or semi-automated techniques. The spectrometric analysis is performed using an Applied Biosystems Voyager MALDI-TOF-MS (Foster City, Calif.). The primary proteins from each fraction are identified and the significant differences in spectra between muscle fractions from wild type and mutant strains that reflect the absence of the target protein, as well as any pleiotropic reduction, accumulation, and post-translational modifications of other proteins in the proteome, are noted.

Invertebrate Muscle (Fruit Flies). To illustrate the potential of protein analysis using the methods and devices described in the invention, changes in the muscle cytomatrix proteome that arise from a deletion or a single point mutation of a target phosphoprotein (myosin regulatory light chain: RLC), or the kinase responsible for phosphorylating the protein (myosin regulatory light chain kinase: MLCK) are investigated. RLC phosphorylation modulates muscle contraction in *Drosophila* (Maughan and Vigoreaux, 1999) and other species. Single flight muscle fibers are obtained from adult (2–5 day) wild type (+/+) or mutant (RLC–/+ (Warmke et al., 1992), MLCK–/–, and RLC[S66A,S67A]/ [S66A,S67A] (Tohtong et al., 1997) flies. The mutants represent classes of diseases that can occur from point mutations in nucleotide or amino acid sequence.

Single muscle fibers from the indirect flight muscles are isolated and skinned under oil, according to the methods described in the examples above. Subcellular fractionation of proteins, single bead chromatography, and MALDI-TOF analysis (using standard procedures) of the fractionated sample aliquots is carried out as described in Examples 1 and 2. The primary proteins from each fraction are identified and the significant differences in spectra between fractions from normal and mutant muscle that reflect differences in protein accumulation and post-translational modifications are noted.

The following is demonstrated: 1) a reduced accumulation of target protein in the hetrozygote null mutant (myosin regulatory light chain: RLC–/+), 2) an absence of target protein in the homozygous null mutant (myosin regulatory light chain kinase: MLCK–/–), 3) a post-translational modification of the target protein (absence of phosphorylation of Ser 66 and Ser 67 of the regulatory light chain) produced by amino acids substitutions in the conserved MLCK-dependent phosphorylation site in the target protein (RLC[S66A, S67A]/[S66A,S67A]), and 4) a post-translational modification of the target protein (reduced phosphorylation of Ser 66 and Ser 67 of the regulatory light chain) produced by deleting the accessory protein (MLCK) that is partly or wholly responsible for phosphorylating the target protein.

Vertebrate Muscle (Mice). To further illustrate the potential of protein analysis in animal models of human diseases using the methods and devices described in the invention, changes in the muscle proteome of a mouse model of human muscular dystrophy are investigated. Adult (6–8 week) wild type (dy/+ or +/+) or dystrophic (dy/dy) 129 mice are raised from breeding pairs obtained from Jackson Laboratories, Bar Harbor, Me., and housed in the AALAC-accredited Given Animal Care Facility at the University of Vermont.

Single muscle fibers from the extensor digitorum longus (which contain predominately fibers of the fast twitch type) are isolated and skinned under oil, according to the methods described in the examples above. Subcellular fractionation of proteins, single bead chromatography, and MALDI-TOF analysis of the fractionated sample aliquots are carried out as described in Examples 1 and 2 above as in the invertebrate studies and using standard MALDI procedures. The primary proteins from each fraction are identified and the significant differences in spectra between normal and dystrophic mouse muscle fractions that reflect accumulation and post-translational modifications of proteins are noted. Reduction in accumulation or modification of wild-type dystrophin present in the initial fraction (saponin treatment) of dy/dy mice is consistent with changes reported in previous studies. Further, any changes in accumulation of parvalbumin, a soluble $Ca^{2+}$— and $Mg^{2+}$—binding protein found in relatively high concentrations in fast twitch skeletal muscles of vertebrates, parallels changes in $^{45}Ca$ accumulation. Parallel changes support the hypothesis that a change occurs in the membrane permeability (leak channel) or active transport of ions in the dystrophic mouse muscle (Lipicky & Hess, 1974), thereby producing a chronic increase in $^{45}Ca$ accumulation (Bodensteiner & Engel, 1978) leading to a dystrophic condition via Ca-activated proteases (Alderton & Steinhardt, 2000). This condition could be muted or partially compensated by a triggered increase in synthesis and accumulation of the soluble $Ca^{2+}$-binding protein parvalbumin.

7.4 Example 4

Characterization of Variability of Spectra of Polypeptides Obtained from Subcellular Fractionation and Single Sephadex Bead Chromatography.

Summary. In experiments associated with those described in Example 3, the instrumental and experimental variability of the polypeptide spectra are examined, i.e., a study akin to that described in Example 2 for elemental analysis. Spectra (amplitudes and mass/charge ratios) of polypeptides at two levels in the system are compared: 1) between similar aliquots (assessing instrumental variability) and 2) between similar PMUs (assessing experimental variability). The prominent spectral peaks are integrated, and the coefficient of variation of each peak area and the amplitude of each peak are taken as measures of reproducibility at each system level.

Materials and Methods. Optimal calibration of the system is determined by hydrating the Sephadex beads with solutions containing $CoCl_2$ and other molecular species of interest at specified concentrations (e.g., 5 mM $CoCl_2$, 0–150 mM K, and 0–2 mM parvalbumin). Spectral peaks corresponding to the element or polypeptide (e.g., $^{39}K$ and $^{41}K$, fragmentation products or tryptic digests of $^{11,600}$Parvalbumin) are integrated and each integrated area divided by that of $^{39}Co$. A calibration plot (ratio of integrated peaks of each species to that of Co versus concentration of each species) is constructed and regression analysis performed. By comparing ratios of integrated peaks from, e.g., a 5 mM Co-doped cytosolic sample bead with the those of the other species in the calibration plots, the concentration of each specie of interest in the cytosolic sample is calculated (see Example 3 above). This calibration procedure is corroborated by using strontium ($^{88}Sr$), an element, like Co, that is present in only trace amounts in muscle.

8. REFERENCES CITED

Various publications are cited throughout the specification. The entire disclosure of each such reference is incorporated herein by reference, including without limitation, the disclosures of each of the following references.

Bodensteiner J B, Engel A G. 1978. Intracellular calcium accumulation in Duchenne dystrophy and other myopathies: A study of 567,000 muscle fibers in 114 biopsies. *Neurology* 28:439–446.

Cahill D J, Nordhoss E, O'Bren J, Klose J, Eickhoff H, Lehrach H. 2001. Bridging genomic and proteomics, in: *Proteomics: From Peptide Sequence to Function*, Pennington S R, Dunn M J, eds., Bios Scientific Publishers, Oxford, 1–22.

Godt R E, Good P, Maughan D, Perl D, Tanner B. 1985. Cytosol constituents from frog skeletal muscle determined by laser microprobe mass analysis. *J. Physiol.* (London) 160P.

Godt R E, Maughan D W. 1988. On the composition of the cytosol of relaxed skeletal muscle of the frog. *Am. J. Physiol.* (*Cell Physiol.*) 254:C591–C604.

Hill A V. 1965. *Trails and trials in physiology*. Edward Arnold, London.

Lipicky R J, Hess J. 1974. Potassium permeability in isolated skeletal muscle from mice with muscular dystrophy. *Am. J. Physiol* 226:592–596.

Maughan D, Vigoreaux J. 1999. An integrated view of insect flight muscle: genes, motor molecules, and motion. *News Physiol. Sci.* 14:87–92.

Maughan D W, Molloy J E, Brotto M A P, Godt R E. 1995. Approximating the isometric force-calcium relation of intact frog muscle using skinned fibers. *Biophys. J* 69:1484–1490.

Pandey A, Mann M (2000) Proteomics to study genes and genomes. *Nature* 15: 837–46.

Pennington S R, Dunn M J (2001) eds., *Proteomics: From Peptide Sequence to Function*, Bios Scientific Publishers, Oxford.

Tohtong R, Yamashita M, Graham M, Haeberle J, Simcox A, and Maughan D (1995) Impairment of flight ability and flight muscle function caused by mutations of phosphorylation sites of myosin regulatory light chain in *Drosophila*. *Nature* 374: 650–3.

Warmke J, Yamakawa M, Molloy J E, Falkenthal S, Maughan D W. 1992. A myosin light chain-2 mutation affects flight, wing beat frequency and indirect flight muscle contraction kenetics in *Drosophila*. *J. Cell Biol.* 119:1523–1536.

Alderton, J. M., Steinhardt, R. A. 2000, How calcium influx through calcium leak channels is responsible for the elevated levels of calcium-dependent proteolysis in dystrophic myotubes. *Trend Cardiovasc Med.* 10(6):268–72.

We claim:

1. A method for fractionating a tissue sample to separate a fraction of cellular components from the tissue sample, the method comprising:
   (a) providing a perforated perfusion chamber;
   (b) placing a tissue sample in the chamber, wherein the sample is held in the chamber;
   (c) exposing the tissue sample in the chamber to a fractionating solution by:
      (i) flowing the fractionating solution into the chamber though and/or around the sample at a rate calculated to permit fractionation of the sample; or
      (ii) flowing the fractionating solution into the chamber and maintaining the solution in the chamber for a time sufficient to permit fractionation of the sample,
   (d) concurrently with (c)(i) or following (c)(ii), flowing the fractionating solution out of the chamber to form a bubble or droplet of solution or an array of bubbles or droplets under oil, the fractionating solution comprising the fraction of the cellular components of the tissue sample, wherein the remainder of the tissue sample is held in the chamber.

2. The method of claim 1 wherein the tissue sample has a mass which is less than 1 mg.

3. The method of claim 1 wherein the tissue sample of has a mass which is less than 0.1 mg.

4. The method of claim 1 further comprising enriching polypeptide content of the fractionating solution after it leaves the chamber by removing water therefrom.

5. The method of claim 4 wherein the water is removed using a polymeric matrix unit which absorbs water without absorbing polypeptides.

6. The method of claim 1 wherein steps 1(c) and 1(d) are repeated using fractionation solutions which extract different cellular components.

7. The method of claim 1 wherein one or more of the steps is automated.

8. The method of claim 1 wherein one or more of the steps is performed robotically.

9. The method of claim 1 wherein steps 1(c) and 1(d) are repeated using two or more fractionating solutions selected from the group consisting of:
   (a) a fractionating solution which solubilizes plasma membrane while leaving membranes of intracellular organelles intact, permitting cytosolic polypeptides to diffuse out of cells of the tissue sample and to be separated from non-cytosolic cellular material;
   (b) a fractionating solution which solubilizes membranes of organelles, permitting organellar polypeptides to diffuse out of cells of the tissue sample and to be separated from non-organellar cellular material; and
   (c) a fractionating solution which solubilizes cytomatrix polypeptides permitting cytomatrix polypeptides to be separated from non-cytomatrix cellular material.

10. The method of claim 9 wherein the fractionating solution of 9(a) comprises a detergent component.

11. The method of claim 10 wherein the detergent component comprises saponin.

12. The method of claim 9 wherein the solution of 9(b) comprises a detergent.

13. The method of claim 12 wherein the detergent component comprises triton X100.

14. The method of claim 9 wherein the solution of 9(c) comprises urea.

* * * * *

UNITED STATES PATENT AND TRADEMARK OFFICE
CERTIFICATE OF CORRECTION

| | | |
|---|---|---|
| PATENT NO. | : 7,172,739 B2 | Page 1 of 1 |
| APPLICATION NO. | : 10/154443 | |
| DATED | : February 6, 2007 | |
| INVENTOR(S) | : David W. Maughan | |

It is certified that error appears in the above-identified patent and that said Letters Patent is hereby corrected as shown below:

Claim 1, column 28, line 42 should read as shown below.
--through and/or around the sample at a rate calculated--

Signed and Sealed this

Third Day of April, 2007

JON W. DUDAS
*Director of the United States Patent and Trademark Office*